(12) United States Patent
Marczyk

(10) Patent No.: US 7,543,730 B1
(45) Date of Patent: Jun. 9, 2009

(54) SEGMENTED DRIVE MEMBER FOR SURGICAL INSTRUMENTS

(75) Inventor: Stanislaw Marczyk, Stratford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/144,741

(22) Filed: Jun. 24, 2008

(51) Int. Cl.
*A61B 17/068* (2006.01)

(52) U.S. Cl. .................. 227/175.1; 227/19; 227/176.1; 606/139; 606/219

(58) Field of Classification Search .................. 227/19, 227/176.1, 175.1, 180.1; 606/139, 219, 153, 606/170; 74/502.3, 502.4
See application file for complete search history.

(56) References Cited

U.S. PATENT DOCUMENTS

| | | | |
|---|---|---|---|
| 3,217,557 A * | 11/1965 | Martinot | 74/502.4 |
| 3,452,615 A * | 7/1969 | Gregory, Jr. | 74/502.3 |
| 4,473,077 A * | 9/1984 | Noiles et al. | 227/179.1 |
| 4,646,745 A * | 3/1987 | Noiles | 227/178.1 |
| 5,271,543 A * | 12/1993 | Grant et al. | 227/179.1 |
| 5,312,023 A | 5/1994 | Green et al. | |
| 5,381,943 A | 1/1995 | Allen et al. | |
| 5,456,401 A | 10/1995 | Green et al. | |
| 5,485,952 A | 1/1996 | Fontayne | |
| 5,540,375 A | 7/1996 | Bolanos et al. | |
| 5,601,224 A | 2/1997 | Bishop | |
| 5,680,982 A * | 10/1997 | Schulze et al. | 227/175.1 |
| 5,690,269 A | 11/1997 | Bolanos et al. | |
| 5,704,534 A | 1/1998 | Huitema et al. | |
| 5,713,505 A | 2/1998 | Huitema | |
| 5,725,536 A | 3/1998 | Oberlin et al. | |
| 5,820,009 A | 10/1998 | Melling et al. | |
| 5,823,066 A | 10/1998 | Huitema et al. | |
| 5,849,011 A * | 12/1998 | Jones et al. | 606/47 |
| 5,868,760 A * | 2/1999 | McGuckin, Jr. | 606/139 |
| 5,901,895 A | 5/1999 | Heaton et al. | |
| 6,010,054 A | 1/2000 | Johnson et al. | |
| 6,500,189 B1 * | 12/2002 | Lang et al. | 606/170 |
| 6,663,641 B1 | 12/2003 | Kovac et al. | |
| 6,786,382 B1 | 9/2004 | Hoffman | |
| 6,877,647 B2 | 4/2005 | Green et al. | |
| 7,000,819 B2 * | 2/2006 | Swayze et al. | 227/176.1 |
| 7,083,075 B2 * | 8/2006 | Swayze et al. | 227/176.1 |
| 7,229,456 B2 * | 6/2007 | Lang et al. | 606/170 |
| 2005/0006431 A1 | 1/2005 | Shelton, IV et al. | |
| 2005/0006432 A1 | 1/2005 | Racenet et al. | |
| 2005/0096694 A1 | 5/2005 | Lee | |
| 2005/0273084 A1 | 12/2005 | Hinman et al. | |
| 2005/0279804 A1 | 12/2005 | Scirica et al. | |
| 2006/0011699 A1 | 1/2006 | Olson et al. | |
| 2006/0016853 A1 | 1/2006 | Racenet | |
| 2006/0025817 A1 | 2/2006 | Ortiz et al. | |
| 2006/0047308 A1 | 3/2006 | Ortiz et al. | |
| 2006/0049229 A1 | 3/2006 | Milliman et al. | |
| 2007/0023477 A1 | 2/2007 | Whitman et al. | |
| 2007/0175956 A1 | 8/2007 | Swayze et al. | |

* cited by examiner

*Primary Examiner*—Scott A. Smith

(57) ABSTRACT

A surgical instrument having a segmented drive member is provided. The instrument includes a handle portion, an elongated body portion extending distally from the handle portion and defining a longitudinal axis, a tool assembly mounted on a distal end of the body portion, and a drive member operably connecting the handle portion to the tool assembly. The tool assembly is articulable from a first position along the longitudinal axis to second position. The drive member is configured for actuating the tool assembly in at least the first and second position. The drive member includes a flexible band having first and second surfaces and a plurality of segments mounted on at least the first surface of the band.

12 Claims, 36 Drawing Sheets

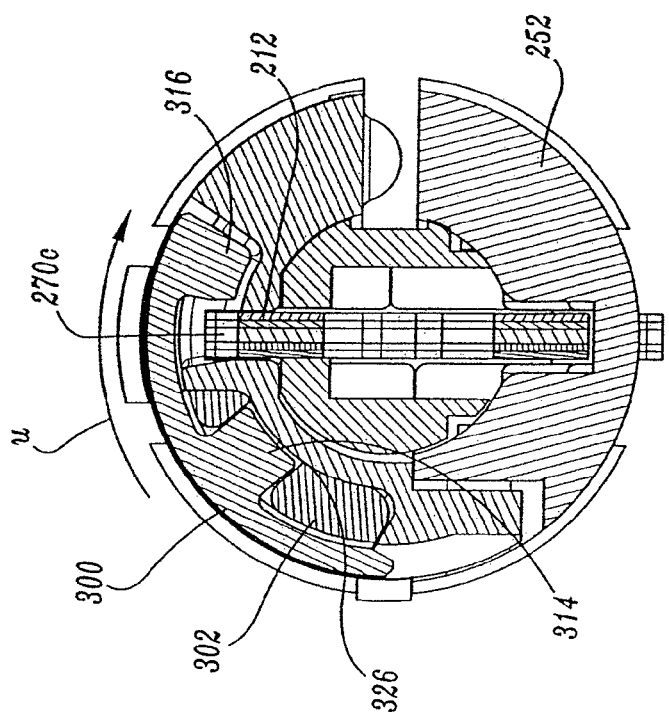
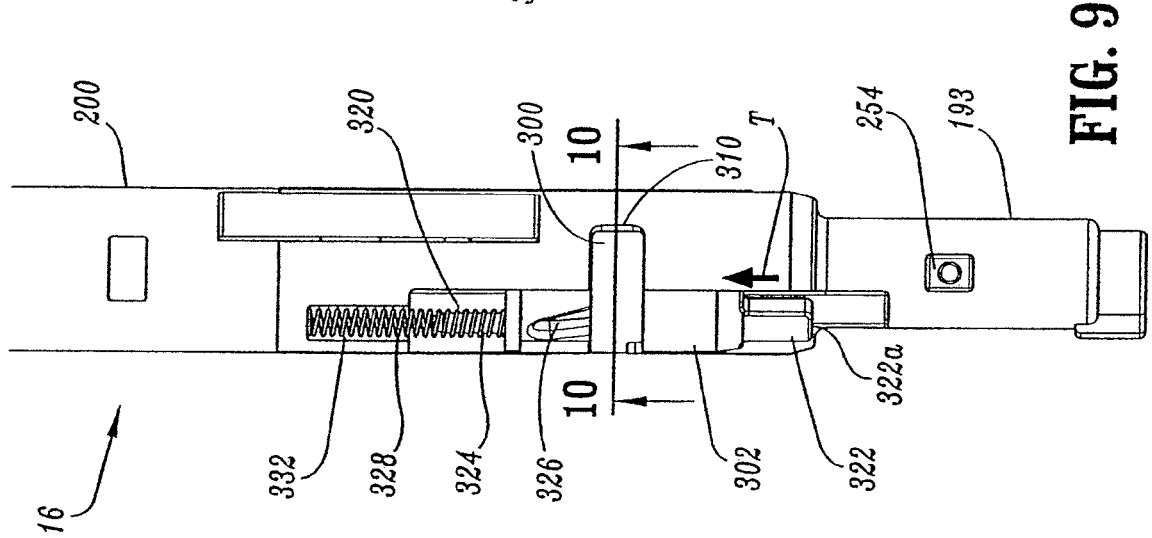
FIG. 10
FIG. 9

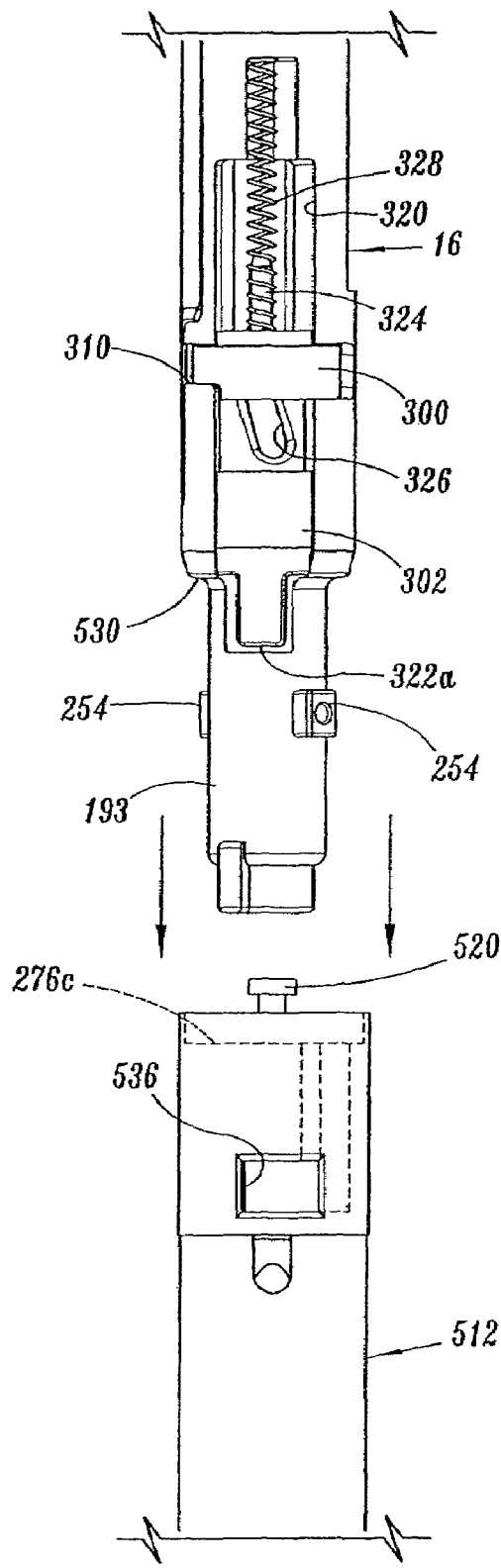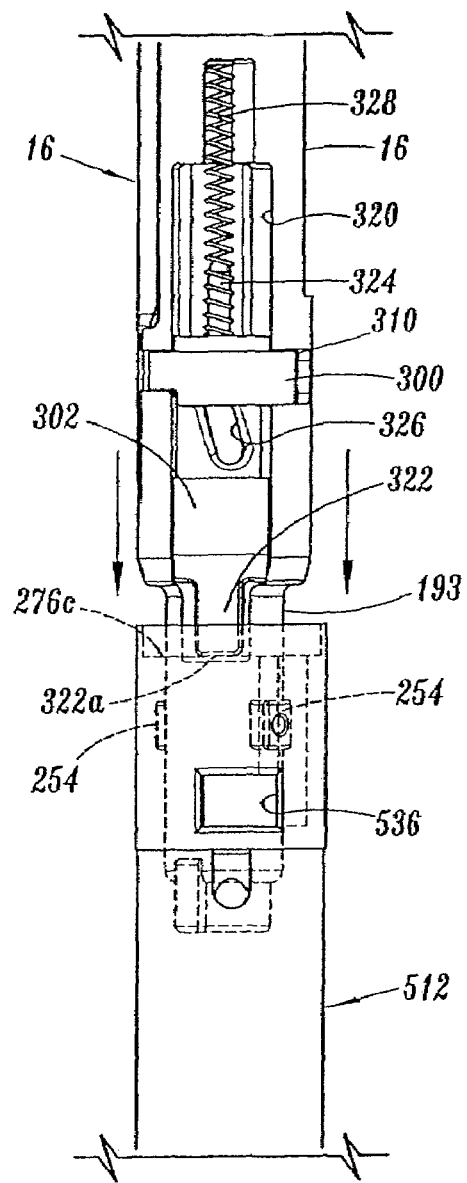
FIG. 12  FIG. 13

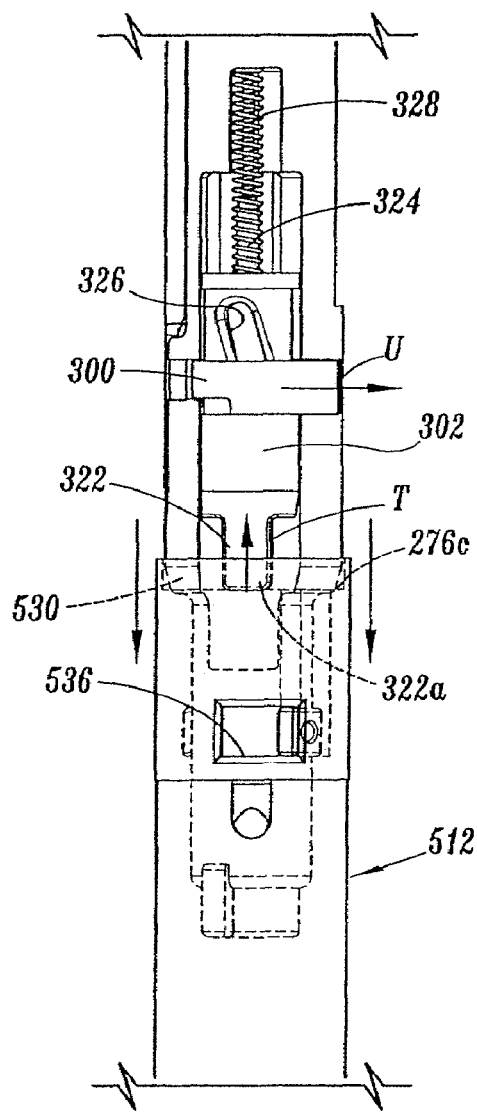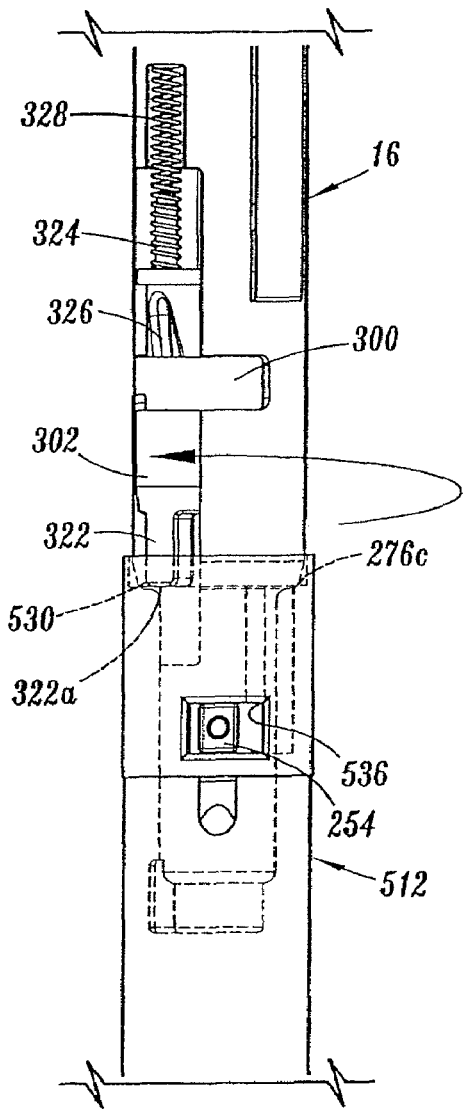
FIG. 14  FIG. 15

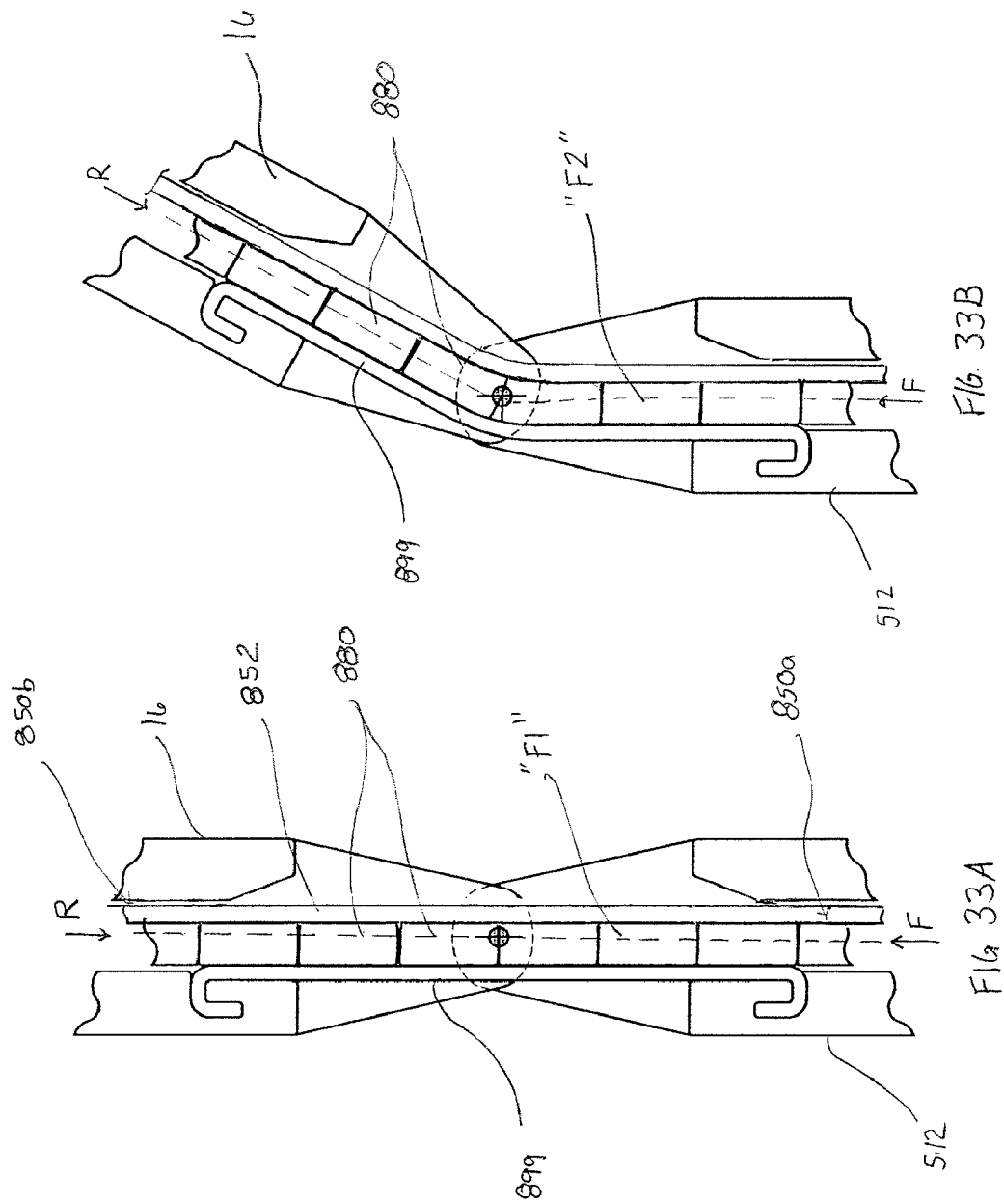

SEGMENTED DRIVE MEMBER FOR SURGICAL INSTRUMENTS

TECHNICAL FIELD

The present disclosure relates to a surgical instrument having articulating tool assemblies. More particularly, the present disclosure relates to a segmented drive member for a surgical instrument having an articulating tool assembly.

BACKGROUND

Surgical instruments which include a tool assembly mounted on a distal end of a body portion of the surgical instrument for articulation are well known. Typically, such surgical instruments include articulation control mechanisms which allow an operator to remotely articulate the tool assembly in relation to the body portion of a surgical instrument to allow the operator to more easily access, operate on, and/or manipulate tissue.

Such articulating tool assemblies have become desirable, especially in the endoscopic surgical procedures. In an endoscopic surgical procedure, the distal end of a surgical instrument is inserted through small incisions in the body to access a surgical site. Typically, a appropriately sized cannula, e.g., 5 mm, 10 mm, etc., is inserted through the body incision to provide a guide channel for accessing the surgical site. Once the distal end of the endoscopic instrument has been received within the body cavity the tool assembly may be articulated.

To activate the tool assembly on the distal end of the surgical instrument in when the tool assembly is in both an articulated and non-articulated position, a drive beam is incorporated into the instrument. The drive beam is generally an elongated flexible member capable of translating lateral movement from the handle assembly to the tool assembly. The flexibility of the drive member permits the tool assembly to be articulated while still maintaining the ability to activate the tool assembly.

The configuration of the flexible drive members makes them susceptible to binding during activation when the tool assembly is in a position other than aligned with the longitudinal axis of the instrument. As the angle between the articulating end and the longitudinal axis approach orthogonal (i.e. 90° from centerline), the likelihood of binding increases. A bound instrument will not function properly and may result in lockout, misfiring, or the like. Furthermore, the limitations imposed by the flexible drive members prevent the articulation joint from being fully articulated to an angle orthogonal to the longitudinal axis formed by the surgical stapler.

Accordingly, it would be desirable to provide a surgical instrument having an articulating tool assembly with an improved drive beam for actuating the tool assembly throughout articulation of the tool assembly.

SUMMARY

Disclosed is a drive beam for use in a surgical instrument. The drive beam includes a flexible band having first and second surfaces and proximal and distal ends. The flexible band may include one or more layers. Mounted on at least one of the first or second surfaces is a plurality of segments or pads.

DESCRIPTION OF THE DRAWINGS

Various embodiments of the presently disclosed surgical instrument are disclosed herein with reference to the drawings, wherein:

FIG. 9 is a top view of the proximal end of the DLU proximal body portion shown in FIG. 1A with the locking mechanism in its unlocked position;

FIG. 10 is a cross-sectional view taken along section lines 10-10 of FIG. 9;

FIG. 12 is a top view of the proximal end of the DLU and the distal end of the surgical instrument shown in FIG. 11 prior to attachment to the distal end of the surgical instrument;

FIG. 13 is a top view of the proximal end of the DLU shown in FIG. 11 as the DLU is advanced linearly into the distal end of the surgical instrument;

FIG. 14 is a top view of the proximal end of the DLU and the distal end of the surgical instrument shown in FIG. 12 after the DLU has been advanced linearly but prior to locking the DLU to the surgical instrument;

FIG. 15 is a top view of the proximal end of the DLU and the distal end of the surgical instrument shown in FIG. 13 after the DLU has been advanced linearly and rotatably locked onto the surgical instrument;

FIG. 33A is a top view of a drive beam according to an embodiment of the present disclosure, in an axially aligned configuration;

FIG. 33B is a top view of the drive beam of FIG. 33A, in an articulated configuration;

DETAILED DESCRIPTION OF EMBODIMENTS

Figure 1:
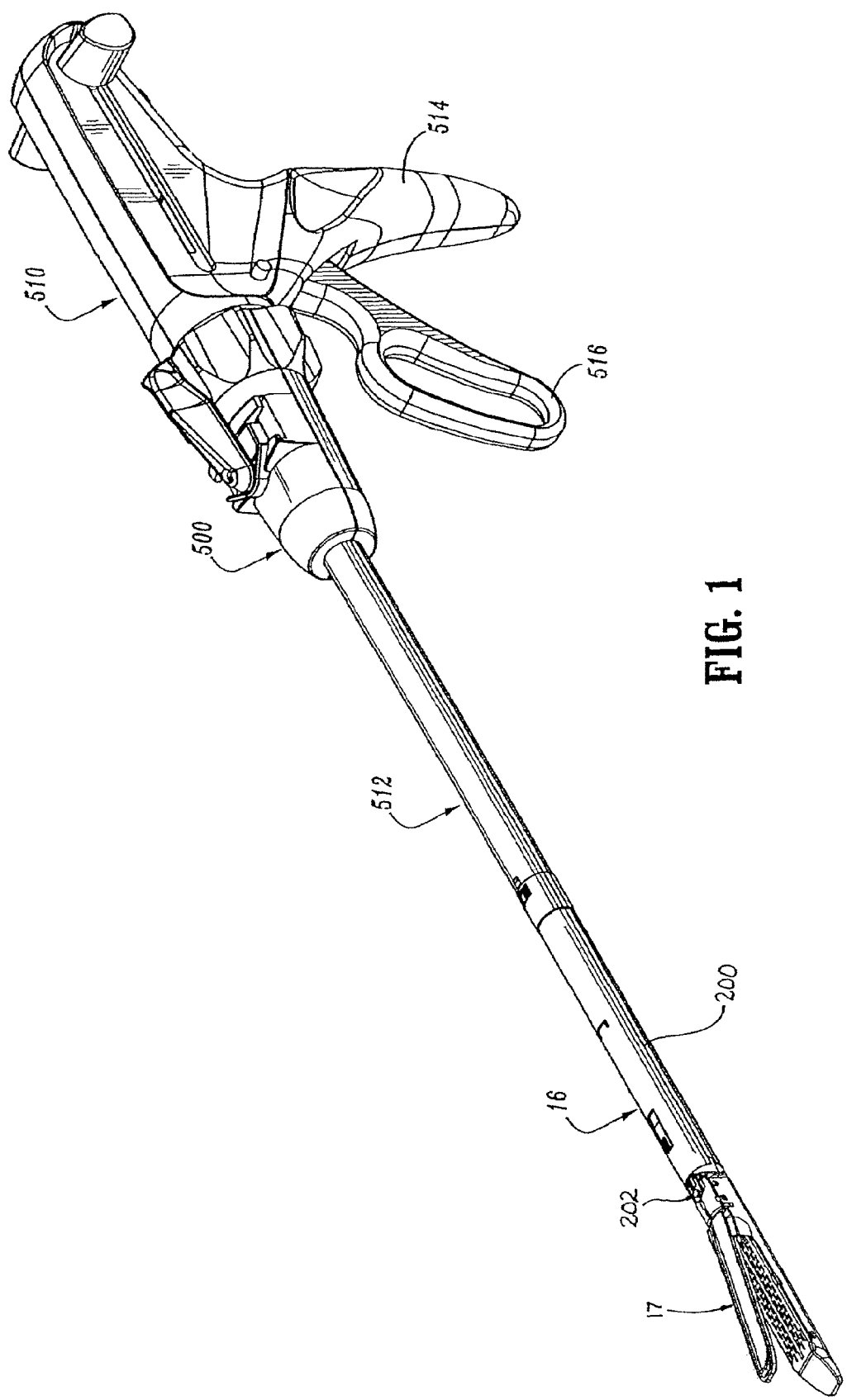
FIG. 1 is a side perspective view from the distal end of one embodiment of the presently disclosed surgical instrument with articulating tool assembly.

Embodiments of the presently disclosed surgical instrument and DLU will now be described in detail with reference to the drawings, in which like reference numerals designate identical or corresponding elements in each of the several views.

Referring to FIG. 1, surgical instrument 500 includes a handle portion 510, a body portion 512, and a disposable loading unit ("DLU") 16. Handle portion 510 includes a stationary handle 514 and a movable handle or trigger 516. Movable handle 516 is movable in relation to stationary handle 514 to advance a control rod 520 which projects from the distal end of body portion 512. Handle portion 510 and body portion 512 may be constructed in the manner disclosed in commonly owned U.S. Pat. No. 6,330,965 to Milliman et al., which is hereby incorporated herein in its entirety by reference. Alternately, other surgical instruments can be used with DLU 16 to perform endoscopic surgical procedures.

Figure 1A:
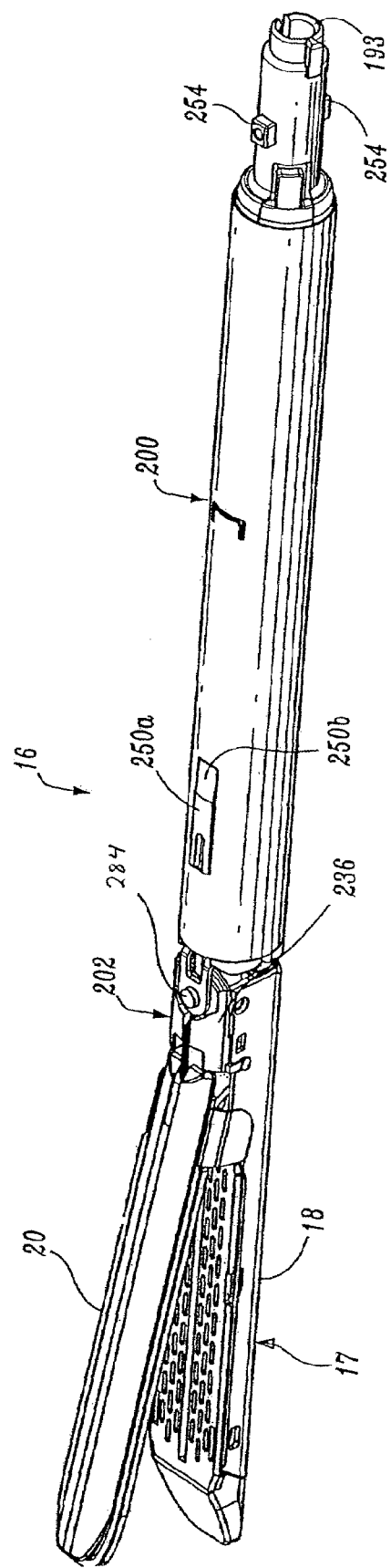
FIG. 1A is a side perspective view from the proximal end of a disposable loading unit (DLU) of the surgical instrument shown in FIG. 1 including the tool assembly.
Figure 11:
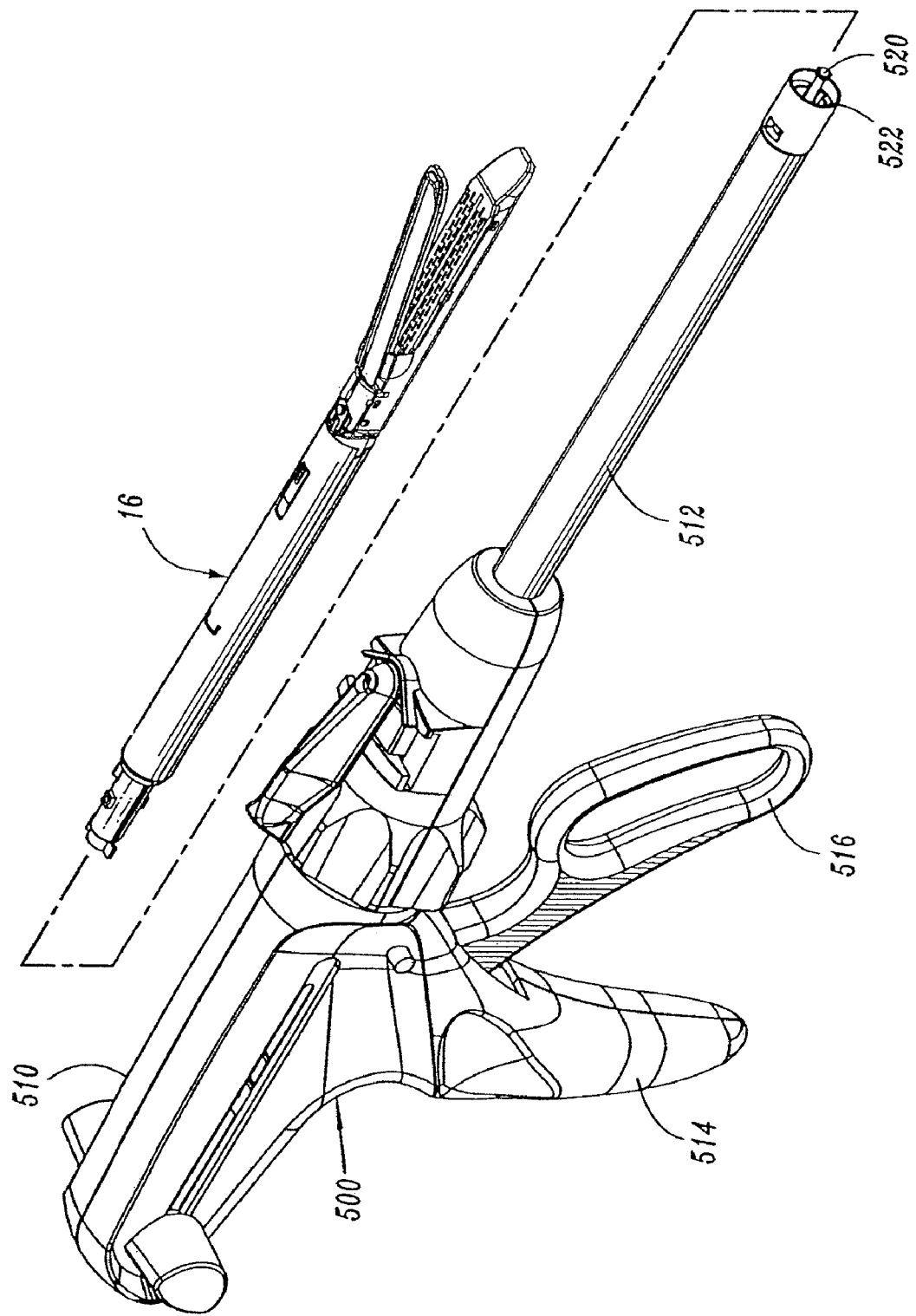
FIG. 11 is a side perspective view of the DLU and surgical instrument shown in FIG. 1 prior to attachment of the DLU to the surgical instrument.

Referring to FIGS. 1 and 1A, briefly, DLU 16 includes a tool assembly 17, a proximal body portion 200 and a mounting assembly 202. Body portion 200 has a proximal end adapted to releasably engage the distal end of a surgical instrument 500 (FIG. 11) in the manner to be discussed in detail below. Mounting assembly 202 is pivotally secured to a distal end of body portion 200 and is fixedly secured to a proximal end of tool assembly 17. Pivotal movement of mounting assembly 202 about an axis perpendicular to a longitudinal axis of body portion 200 affects articulation of tool assembly 17 between a non-articulated position in which the longitudinal axis of tool assembly 17 is aligned with the longitudinal axis of body portion 200 and an articulated position in which the longitudinal axis of tool assembly 17 is disposed at an angle to the longitudinal axis of body portion 200.

Figure 2:
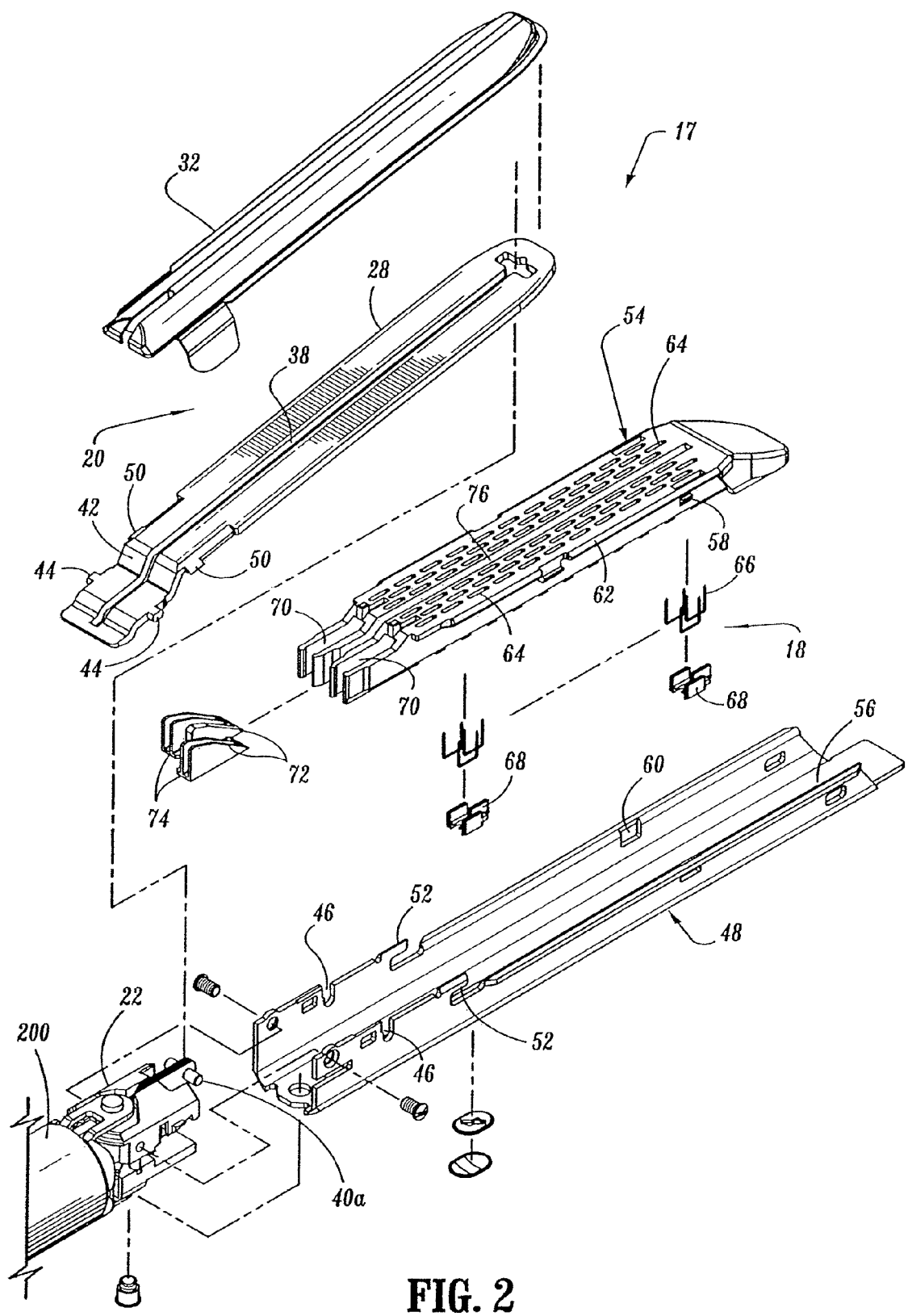
FIG. 2 is a side perspective view of the distal end of mounting assembly and tool assembly, with parts separated, of the DLU of the surgical instrument shown in FIG. 1.
Figure 3:
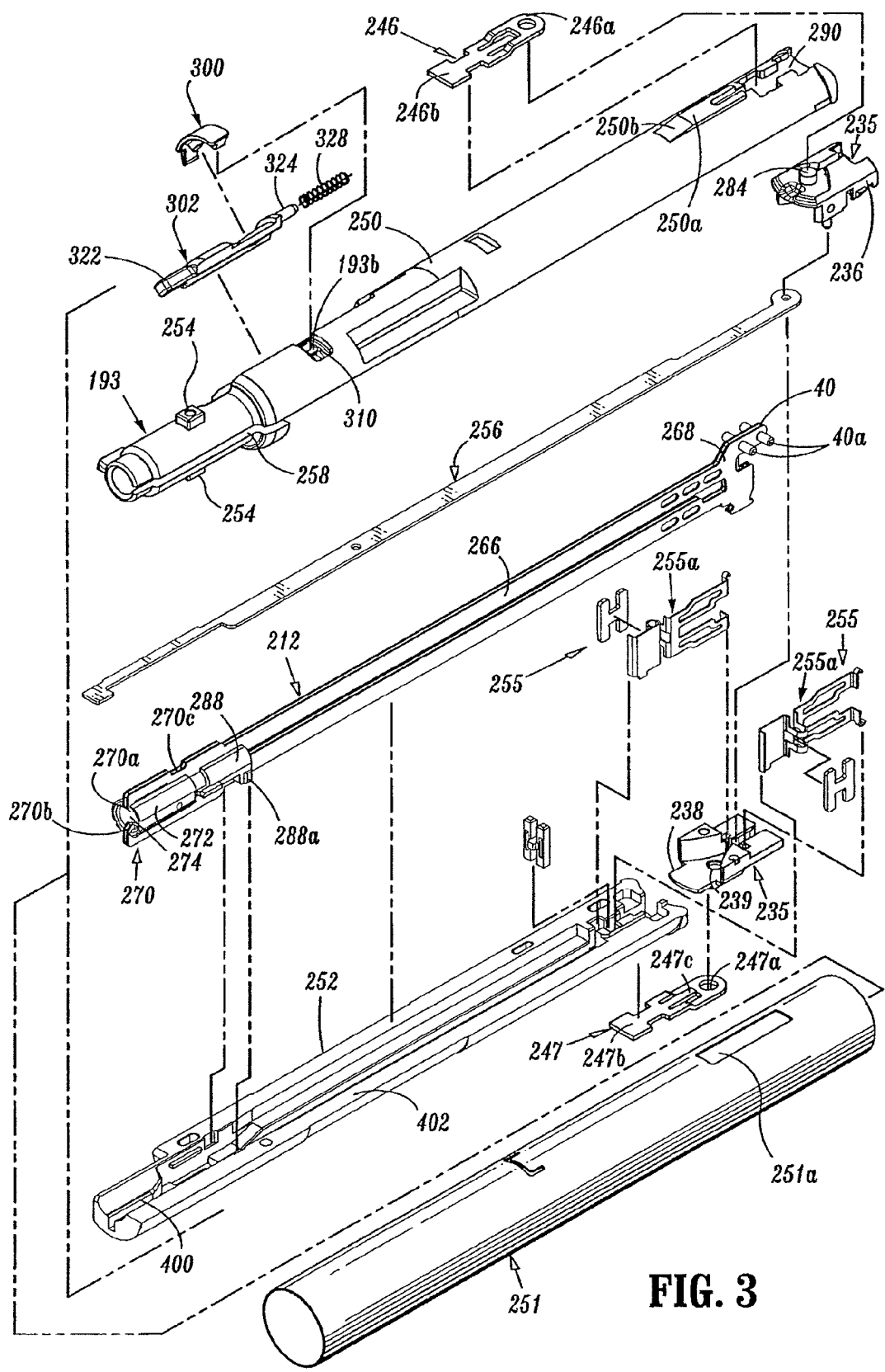
FIG. 3 is a side perspective view of the mounting assembly and the proximal body portion of the DLU shown in FIG. 1A with parts separated.
Figure 4:
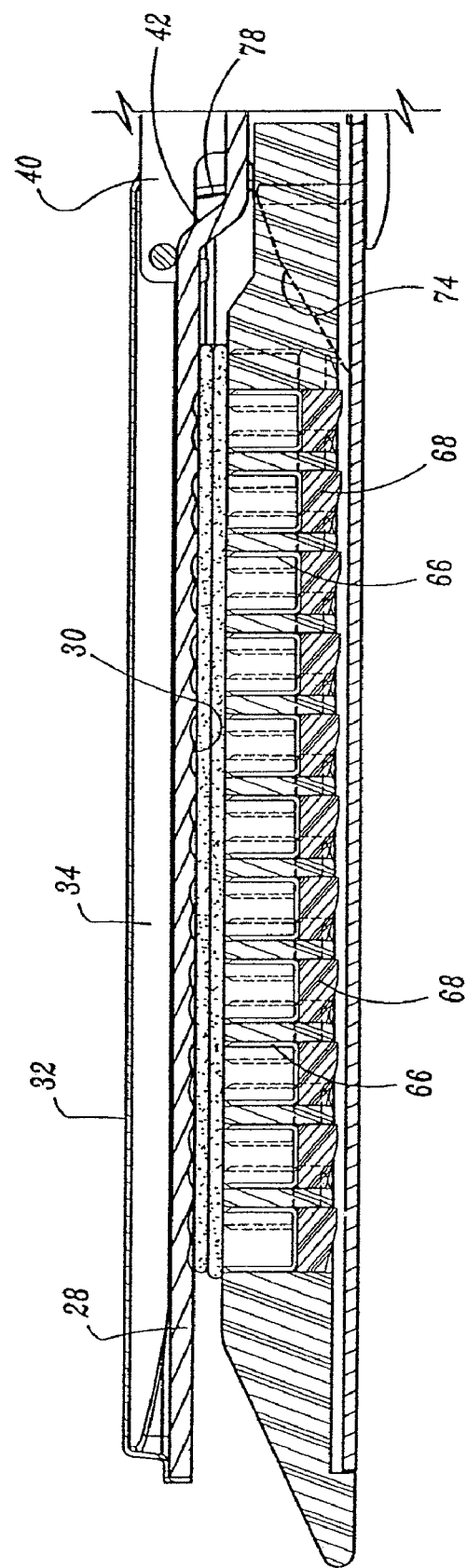
FIG. 4 is a side cross-sectional view of the tool assembly of the DLU shown in FIG. 1A.

Referring to FIGS. 2-4, tool assembly 17 includes a cartridge assembly 18 and an anvil assembly 20. Anvil assembly 20 includes an anvil portion 28 having a plurality of staple deforming concavities 30 (FIG. 4) and a cover plate 32 secured to a top surface of anvil portion 28. Cover plate 32 and anvil portion 28 define a cavity 34 (FIG. 4) therebetween which is dimensioned to receive a distal end of a drive assembly 212 (FIG. 3). Cover plate 32 encloses the distal end of drive assembly 212 to prevent pinching of tissue during actuation of DLU 16. A longitudinal slot 38 extends through anvil portion 28 to facilitate passage of a retention flange 40 of drive assembly 212. A camming surface 42 formed on anvil portion 28 is positioned to engage a pair of cam members 40a supported on retention flange 40 of drive assembly 212 to effect approximation of the anvil and cartridge assemblies. A pair of pivot members 44 are formed. A pair of stabilizing members 50 engage a respective shoulder 52 formed on carrier 48 to prevent anvil portion 28 from sliding axially in relation to staple cartridge 54 as camming surface 42 is pivoted about pivot members 44.

Cartridge assembly 18 includes carrier 48 which defines an elongated support channel 56 which is dimensioned and configured to receive staple cartridge 54. Corresponding tabs 58 and slots 60 formed along staple cartridge 54 and elongated support channel 56, respectively, function to retain staple cartridge 54 at a fixed location within support channel 56. A pair of support struts 62 formed on staple cartridge 54 are positioned to rest on side walls of carrier 48 to further stabilize staple cartridge 54 within support channel 56. Carrier 48 has slots 46 for receiving pivot members 44 of anvil portion 28 and allowing anvil portion 28 to move between spaced and approximated positions.

Staple cartridge 54 includes retention slots 64 (FIG. 2) for receiving a plurality of staples or fasteners 66 and pushers 68. A plurality of laterally spaced apart longitudinal slots 70 extend through staple cartridge 54 to accommodate upstanding cam wedges 72 of an actuation sled 74 (FIG. 2). A central longitudinal slot 76 extends along substantially the length of staple cartridge 54 to facilitate passage of a knife blade 78

(FIG. 4). During operation of surgical stapler 10, drive assembly 212 abuts actuation sled 74 and pushes actuation sled 74 through longitudinal slots 70 of staple cartridge 54 to advance cam wedges 72 into sequential contact with pushers 68. Pushers 68 translate vertically along cam wedges 72 within fastener retention slots 64 and urge fasteners 66 from retention slots 64 into staple deforming cavities 30 (FIG. 4) of anvil assembly 20.

Referring to FIG. 3, mounting assembly 235 includes an upper mounting portion 236 and a lower mounting portion 238. A centrally located pivot member 284 extends from upper mounting portion 236 through a respective opening 246a formed in a first coupling member 246. Lower mounting portion 238 includes a bore 239 for receiving pivot member 284 (see FIG. 3F). Pivot member 284 extends through bore 239 and opening 247a of a second coupling member 247. Each of coupling members 246, 247 includes an interlocking proximal portion 246b, 247b configured to be received in grooves 290 formed in the distal end of an inner housing which is formed from upper and lower housing halves 250 and 252. Coupling members 246, 247 retain mounting assembly 235 and upper and lower housing halves 250 and 252 in a longitudinally fixed position in relation to each other while permitting pivotal movement of mounting assembly 235 in relation thereto.

Figure 3A:
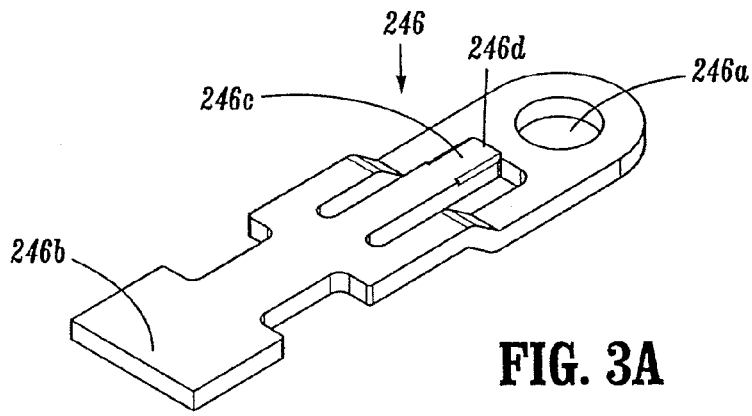
FIG. 3A is a side perspective view of a coupling member of the surgical instrument shown in FIG. 1.
Figure 3B:
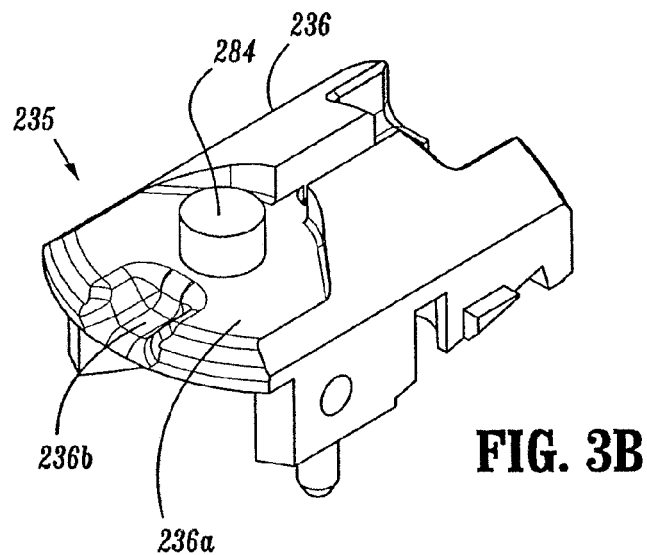
FIG. 3B is a side perspective view of an upper mounting portion of the mounting assembly of the DLU of the surgical instrument shown in FIG. 1.
Figure 3C:
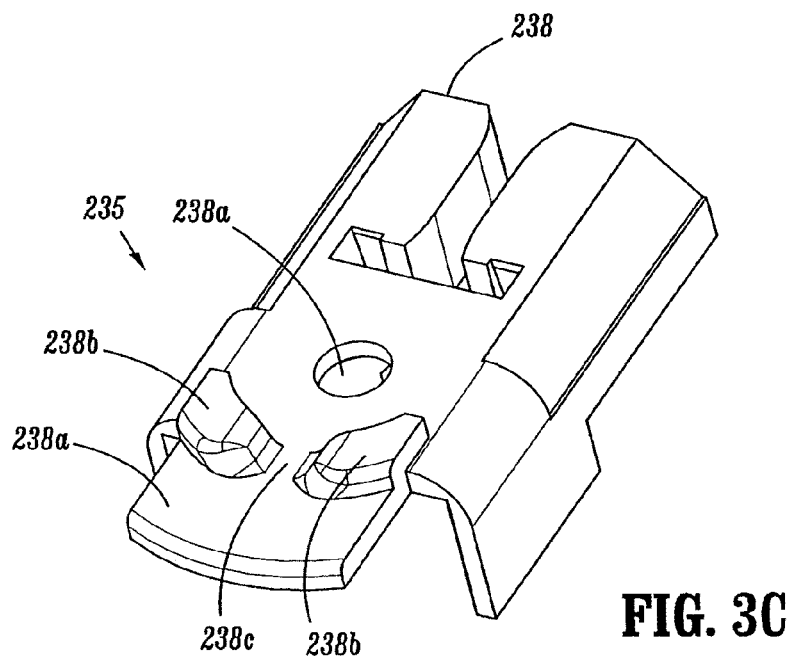
FIG. 3C is a side perspective view of a lower mounting portion of the mounting assembly of the DLU of the surgical instrument shown in FIG. 1.
Figure 3D:
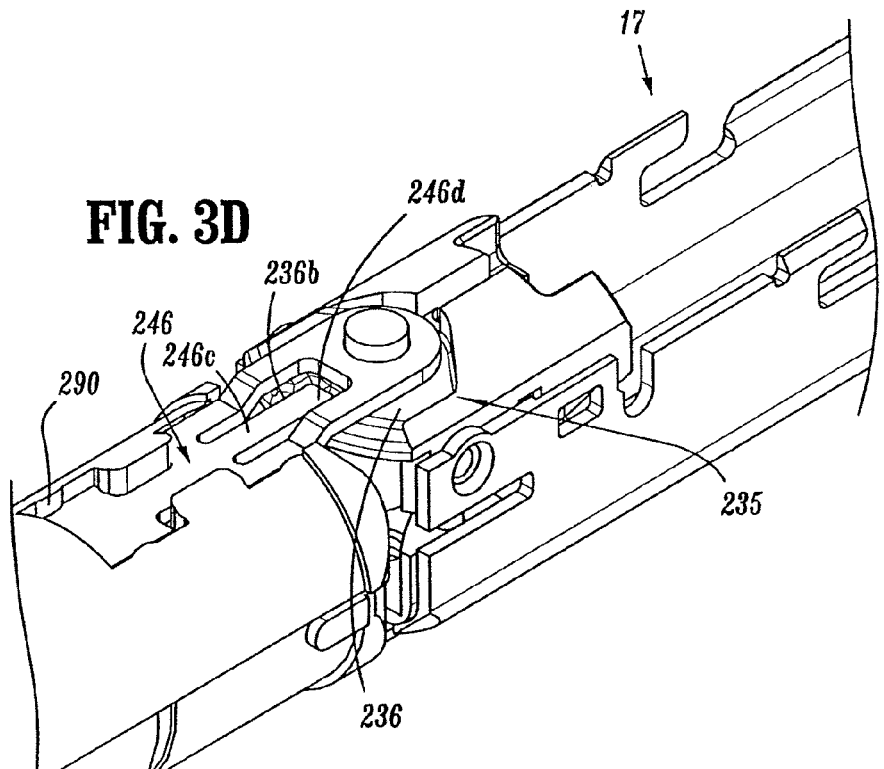
FIG. 3D is a side perspective view from above the proximal body portion, the mounting assembly and the tool assembly of the DLU of the surgical instrument with the tool assembly in its non-articulated position.

Referring to FIGS. 3A-3C, each coupling member 246, 247 includes a cantilevered spring arm 246c which has a distal end 246d positioned to engage mounting assembly 235. More specifically, upper mounting portion 236 includes a top surface 236a which includes a recess 236b dimensioned to receive distal end 246d of spring arm 246c of a respective coupling member 246. Lower mounting portion 238 includes a bottom surface 238a having a pair of raised surfaces 238b which define a recess 238c which is dimensioned to receive spring arm 247c of a respective coupling member 247. Alternatively, at least one recess may be formed in the proximal end of tool assembly 17.

Figure 3E:
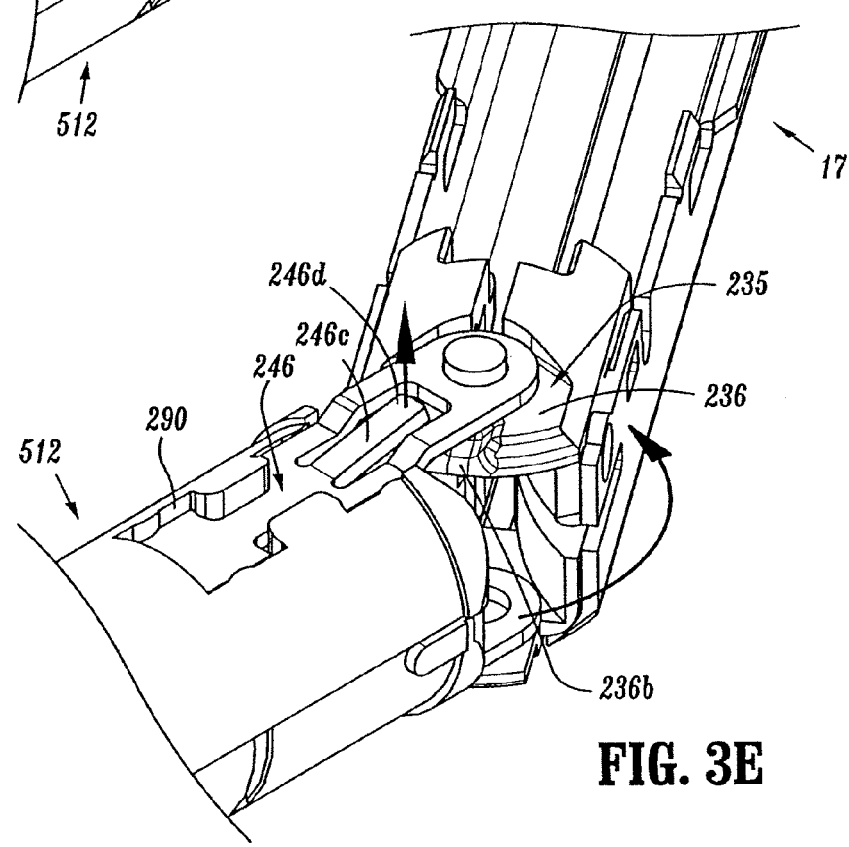
FIG. 3E is a side perspective view from above the proximal body portion, the mounting assembly and the tool assembly shown in FIG. 3D with the tool assembly in an articulated position.
Figure 3F:
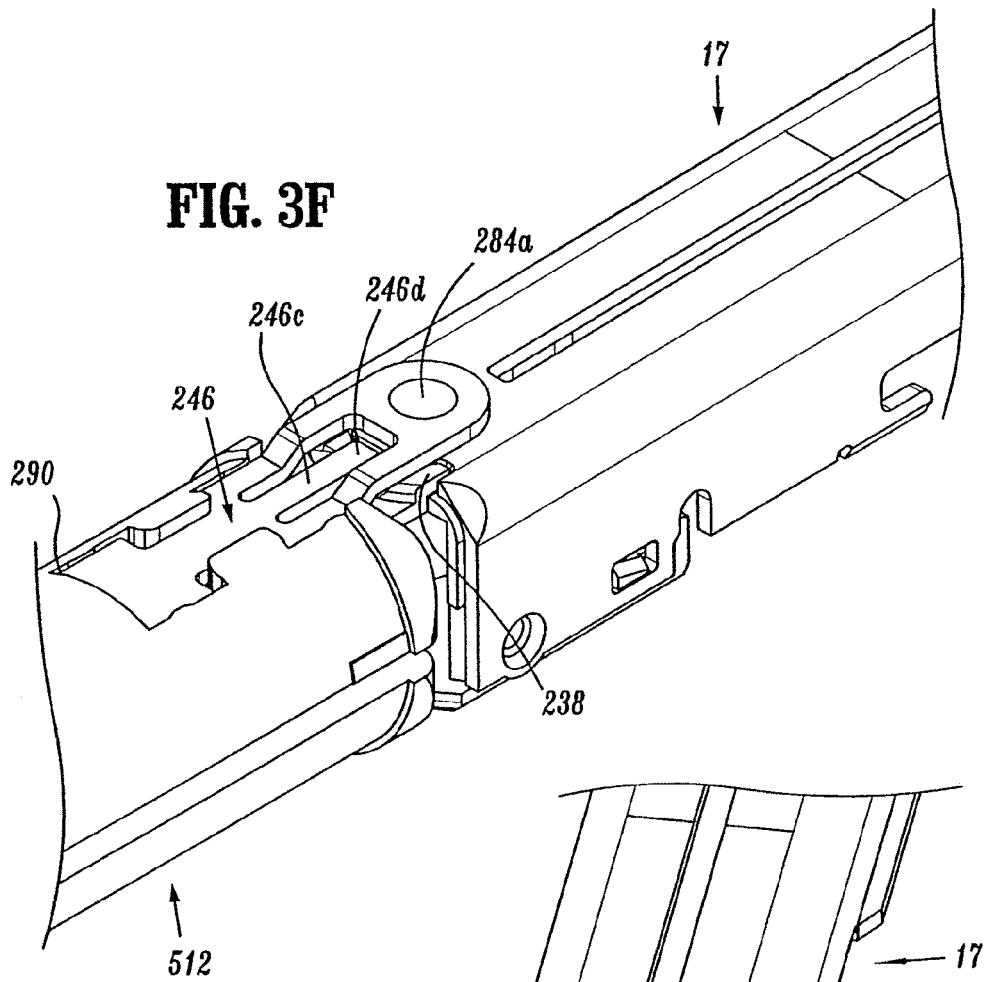
FIG. 3F is a side perspective view from below the proximal body portion, the mounting assembly and the tool assembly of the DLU of the surgical instrument with the tool assembly in its non-articulated position.
Figure 3G:
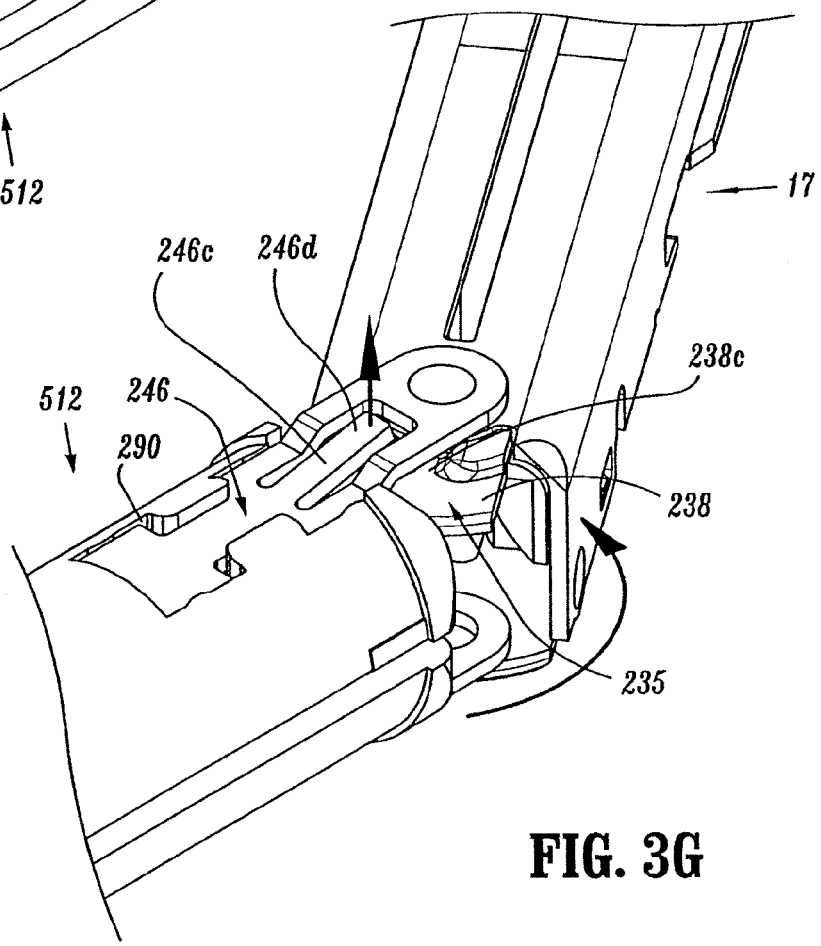
FIG. 3G is a side perspective view from below the proximal body portion, the mounting assembly and the tool assembly shown in FIG. 3F with the tool assembly in an articulated position.

As illustrated in FIGS. 3D-3G, when distal end of spring arms 246c, 247c of coupling members 246, 247 are positioned in recesses 236b and 238c of upper and lower mounting portions 236 and 238, respectively, spring arms 246c, 247c retain mounting assembly 235 in a non-articulated position. Spring arms 246c, 247c will retain mounting assembly 235 in its non-articulated position until a predetermined force sufficient to deflect spring arms 246c from recesses 236b and 238c is applied to effect articulation of mounting assembly 235 and tool assembly 17. When the predetermined force is applied to the mounting assembly 235 and tool assembly 17, spring arms 246c, 247c will spring or deflect outwardly from recesses 236b and 238c, as shown in FIGS. 3E and 3G, to permit pivotal movement of mounting assembly 235 (and, thus, tool assembly 17) in relation to the distal end of proximal body portion 200 of the DLU 16.

As discussed above, spring arms 246c and recesses 236b and 238c maintain tool assembly 17 in its non-articulated position until a predetermined force has been applied to mounting assembly 235 to disengage spring arms 246c, 247c from recesses 236b and 238c of mounting assembly 235. It is envisioned that the spring arms/recesses could be incorporated into any articulating surgical device including staplers, graspers (See FIG. 3H), powered sealing devices, e.g., RF sealing devices, etc. Further, although two spring arms/recesses are shown, a single spring arm can be provided. Moreover, the articulating tool assembly need not form part of a DLU but rather can be supported directly on the distal end of a surgical instrument. For example, the mounting assembly can be removably or irremovably secured to the tool assembly and secured directly to the distal end of a surgical instrument.

Upper housing half 250 and lower housing half 252 are contained within an outer sleeve 251 of body portion 200 (FIG. 3). Body portion 200 includes a cutout 251a dimensioned to receive a boss or projection 250a formed on upper housing half 250. The positioning of projection 250a within cutout 251a prevents axial and rotational movement of upper and lower housing halves 250 and 252 within outer sleeve 251 of body portion 200. In one embodiment, boss 250a has a substantially rectangular configuration having a greater axial dimension than lateral dimension. The greater axial dimension provides increased surface area for preventing rotation of upper and lower housing halves 250 and 252 within sleeve 251. A proximal portion 250b of boss 250a is ramped. Ramped proximal portion 250b allows sleeve 251 to be slid over boss 250a as upper and lower housing halves 250 and 252 are positioned within sleeve 251. It is envisioned that boss 250a may assume other configurations, e.g., circular, square, triangular, etc., and still achieve its intended function. Further, boss 250a can be repositioned anywhere along upper housing half 250 or, in the alternative, be positioned on lower housing half 252 or partly on each housing half 250 and 252.

Figure 7:
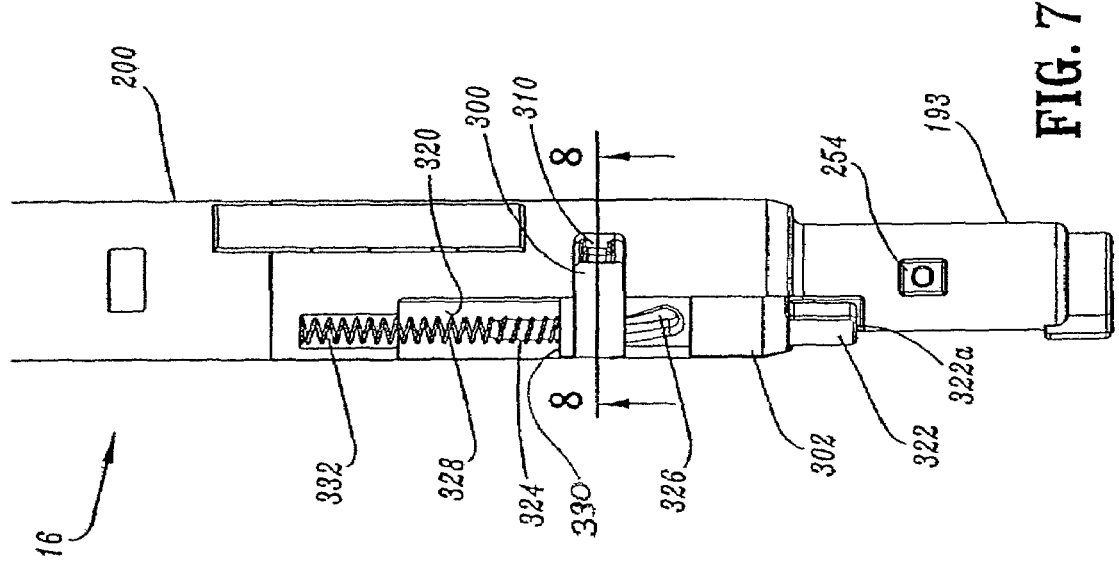
FIG. 7 is a top view of the proximal end of the DLU proximal body portion shown in FIG. 1A with the locking mechanism in its locked position.

The proximal end or insertion tip 193 of upper housing half 250 includes engagement nubs 254 for releasably engaging the distal end of a surgical instrument in a bayonet-type fashion (see FIGS. 1A and 7). Housing halves 250 and 252 define a channel 400 for slidably receiving axial drive assembly 212 therein. An articulation link 256 is dimensioned to be slidably positioned within a slot 402 formed between upper and lower housing halves 250 and 252. A pair of H-block assemblies 255 are positioned adjacent the distal end of housing portion 200 and adjacent the distal end of axial drive assembly 212 to prevent outward buckling and bulging of drive assembly 212 during articulation and firing of surgical stapling apparatus 10. Each H-block assembly 255 includes a flexible body 255a which includes a proximal end fixedly secured to body portion 200 and a distal end fixedly secured to mounting assembly 235 (FIG. 3). Alternatively, blowout plates (not shown) may be positioned adjacent the distal end of housing portion 200 and adjacent the distal end of axial drive assembly 212 to inhibit outward buckling and bulging of drive assembly 212. For detailed discussion of blowout plates and their use in a surgical instrument, refer to commonly owned U.S. Pat. No. 5,865,361 to Milliman et al., which is incorporated herein by reference in its entirety.

A retention member 288 is supported on engagement section 270 of axial drive assembly 212. Retention member 288 includes a pair of fingers 288a which are releasably positioned within slots or recesses 252a formed in lower housing half 252. In operation, when SULU 16 is attached to a surgical instrument and axial drive assembly 212 is actuated by applying a predetermined force to an actuation member 516 of the surgical instrument 500 (FIG. 11), axial drive assembly 212 is advanced distally to move drive assembly 212 and retention member 288 distally. As retention member 288 is advanced distally, fingers 288a are forced from recesses 252a to provide an audible and tactile indication that the surgical instrument has been actuated. Retention member 288 is designed to prevent inadvertent partial actuation of DLU 16, such as during shipping, by maintaining axial drive assembly 212 at a fixed position within DLU 16 until a predetermined axial force has been applied to axial drive assembly 212.

Axial drive assembly 212 includes an elongated drive beam 266 including a distal working head 268 and a proximal engagement section 270. In one embodiment, drive beam 266 is constructed from multiple stacked sheets of material.

Engagement section 270 includes a pair of resilient engagement fingers 270a and 270b which engage a pair of corresponding retention slots formed in drive member 272. Drive member 272 includes a proximal porthole 274 configured to receive distal end of a control rod 520 (FIG. 11) of a surgical instrument when the proximal end of DLU 16 is engaged with the body portion 512 of a surgical instrument 500.

Referring also to FIGS. 5-10, DLU 16 further includes a locking mechanism including a locking member 300 and a locking member actuator 302. Locking member 300 (FIG. 6) is rotatably supported within a longitudinal or axial slot 310 (FIG. 7) formed in a proximal portion of upper housing half 250 of body portion 200 of DLU 16. Locking member 300 is movable from a first position (FIGS. 7 and 8), in which locking member 300 maintains drive assembly 212 in a pre-fired position, to a second position (FIGS. 9 and 10), in which drive assembly 212 is free to move axially.

Figure 6:
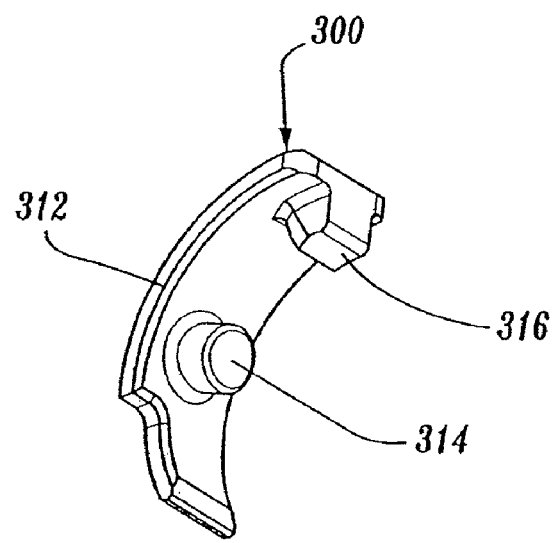
FIG. 6 is a bottom perspective view of a locking member of the locking mechanism shown in FIG. 3.
Figure 8:
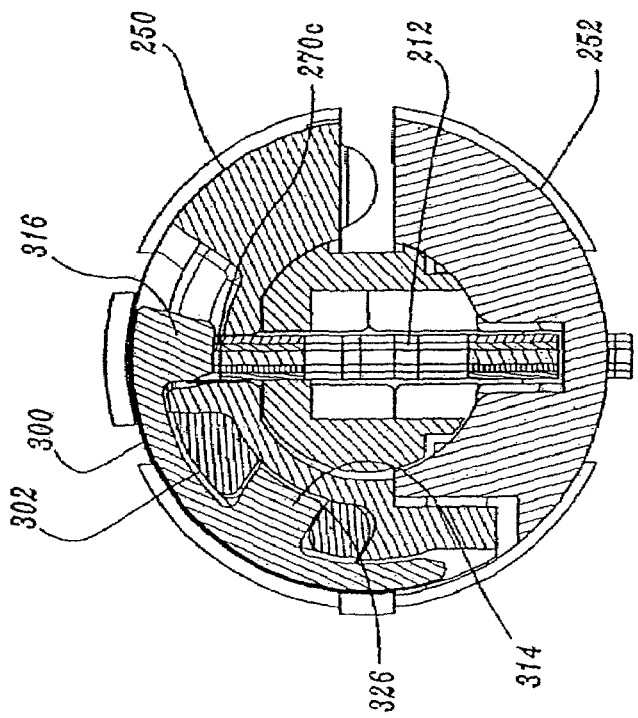
FIG. 8 is a cross-sectional view taken along section lines 8-8 of FIG. 7.

As illustrated in FIG. 6, locking member 300 includes semi-cylindrical body 312 which is slidably positioned within transverse slot 310 formed in upper housing half 250 of body portion 200. Body 312 includes a radially inwardly extending cam member 314 and a radially inwardly extending finger 316. Finger 316 is dimensioned to be slidably received within a notch or slot 270c (FIG. 3) formed in drive assembly 212. Engagement of finger 316 in notch 270c of drive assembly 212 prevents drive assembly 212 from moving linearly within body portion 200 and, thus, prevents actuation of DLU 16.

Figure 5:
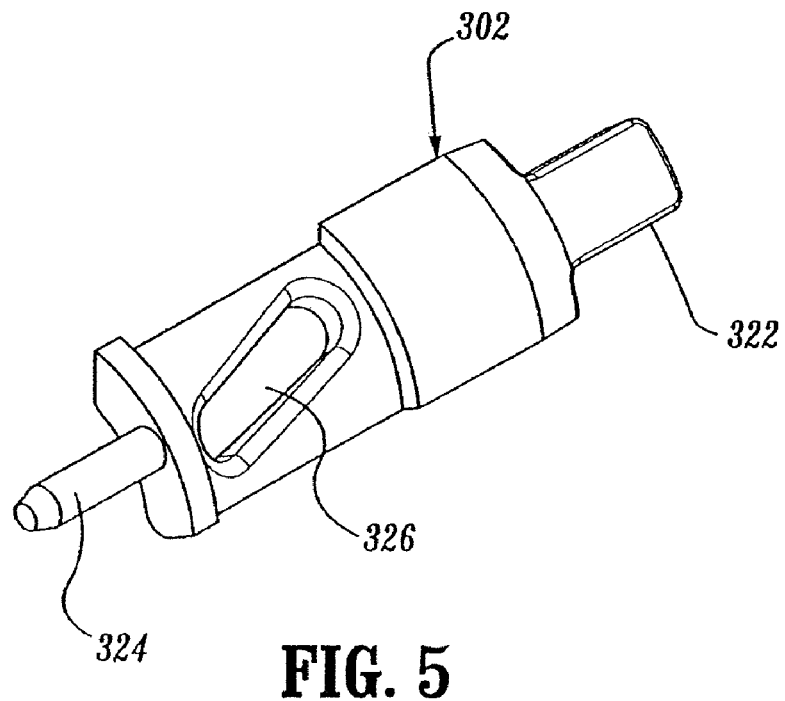
FIG. 5 is a top perspective view of the lock member actuator of the proximal body portion locking mechanism shown in FIG. 3.

Referring to FIGS. 3, 5 and 7, a locking member actuator 302 is slidably positioned within a axial slot 320 (FIG. 7) formed in upper housing half 250 of body portion 200 of DLU 16. Actuator 302 includes a proximal abutment member 322, a distal spring guide 324, and a central cam slot 326. Axial slot 320 intersects transverse slot 310 such that cam member 314 of locking member 300 is slidably positioned within cam slot 326 of locking member actuator 302. A biasing member or spring 328 (FIG. 7) is positioned about spring guide 324 between a distal surface 330 of actuator 302 and a wall 332 (FIG. 7) defining the distal end of axial slot 320. Spring 328 urges actuator 302 to its retracted position within axial slot 320. In its retracted position, abutment member 322 is positioned on and extends radially outwardly of the proximal end of DLU 16 adjacent insertion tip 193 of proximal body portion 200 and axial slot 326 is positioned to locate cam member 314 such that finger 316 of lock member 300 is positioned within notch 270c of drive assembly 212.

FIGS. 11-15 illustrate DLU 16 and surgical instrument 500 prior to and during attachment of DLU 16 to surgical instrument 500. Prior to attachment of DLU 16 onto surgical instrument 500, spring 328 urges actuator 302 to its retracted position to move lock member 300 to its locked position as discussed above. When insertion tip 193 DLU 16 is linearly inserted into the open end 522 (FIG. 11) of the body portion 512 (FIG. 13) of a surgical instrument 500, nubs 254 move linearly through slots (not shown) formed in open end 522 of body portion 512. As nubs 254 pass through the slots, the proximal end 322a of abutment member 322, which is angularly offset from nubs 254, abuts a wall 276c defining the slots for receiving nubs 254. As DLU 16 is moved further into body portion 512, locking member actuator 302 is moved from its retracted position to its advanced position in the direction indicated by arrow "T" in FIG. 14. As actuator 302 is moved to its advanced position, lock member 300 is cammed in the direction indicated by arrow "U" in FIG. 14 from its locked position (FIG. 8) engaged with drive assembly 212 to its unlocked position (FIG. 10) to move finger 316 from notch 270c. The locking mechanism including locking member 300 and locking member actuator 302 prevents accidental or inadvertent advancement or manipulation of the drive member of DLU 16 such as during loading of DLU 16 onto a surgical instrument 500.

When DLU 16 has been moved linearly in relation to instrument 500 to a position wherein a proximal surface 530 of body portion 200 abuts inner surface 276c of body portion 512 (FIG. 15), DLU 16 can be rotated in relation to body portion 512 in a bayonet-type action to position nubs 254 within openings 536 of body portion 512 to lock DLU 16 onto body portion 512. It is envisioned that other coupling types besides bayonet couplings may be used to connect DLU 16 to instrument 500, e.g., spring detent or snap-fit couplings, friction fit couplings, interlocking members, threaded couplings etc.

In an embodiment of the present disclosure illustrated in FIGS. 16-20, a locking assembly 600 is illustrated for use with surgical instrument 500 and disposable loading unit 16 (see FIG. 1, for example). In the illustrated embodiments, locking assembly 600 includes a housing 602, a pusher 604, a rod 606, a slide 608, at least one spring 610, a cam finger 612, a pivot plate 614 having slots 616 and a link 618. Locking assembly 600 generally helps tool assembly 17 (see FIG. 1, for example) maintain its position during firing of surgical instrument 500.

Figure 16:
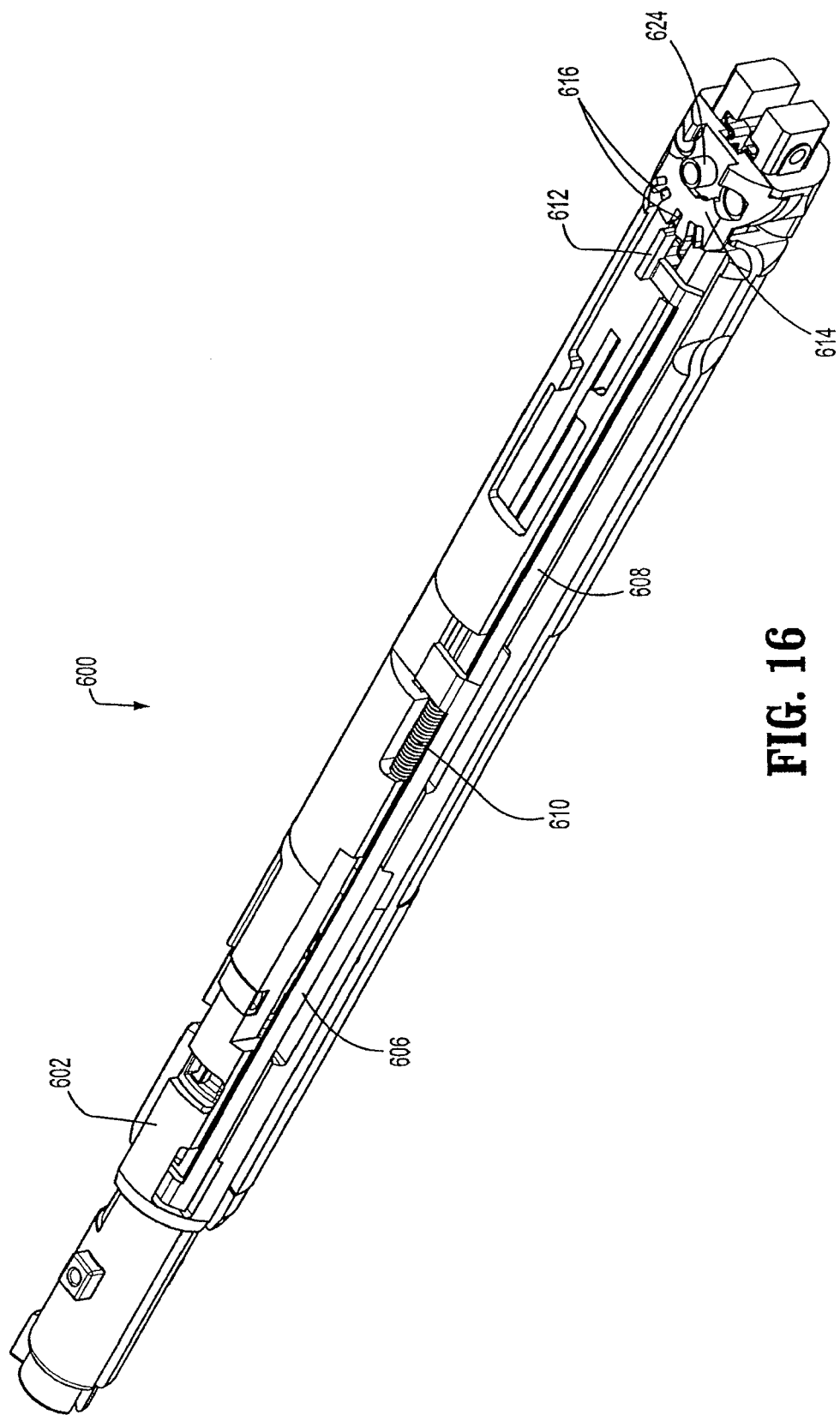
FIG. 16 is a perspective view of a locking assembly for use with a surgical instrument in accordance with an embodiment of the present disclosure.
Figure 17:
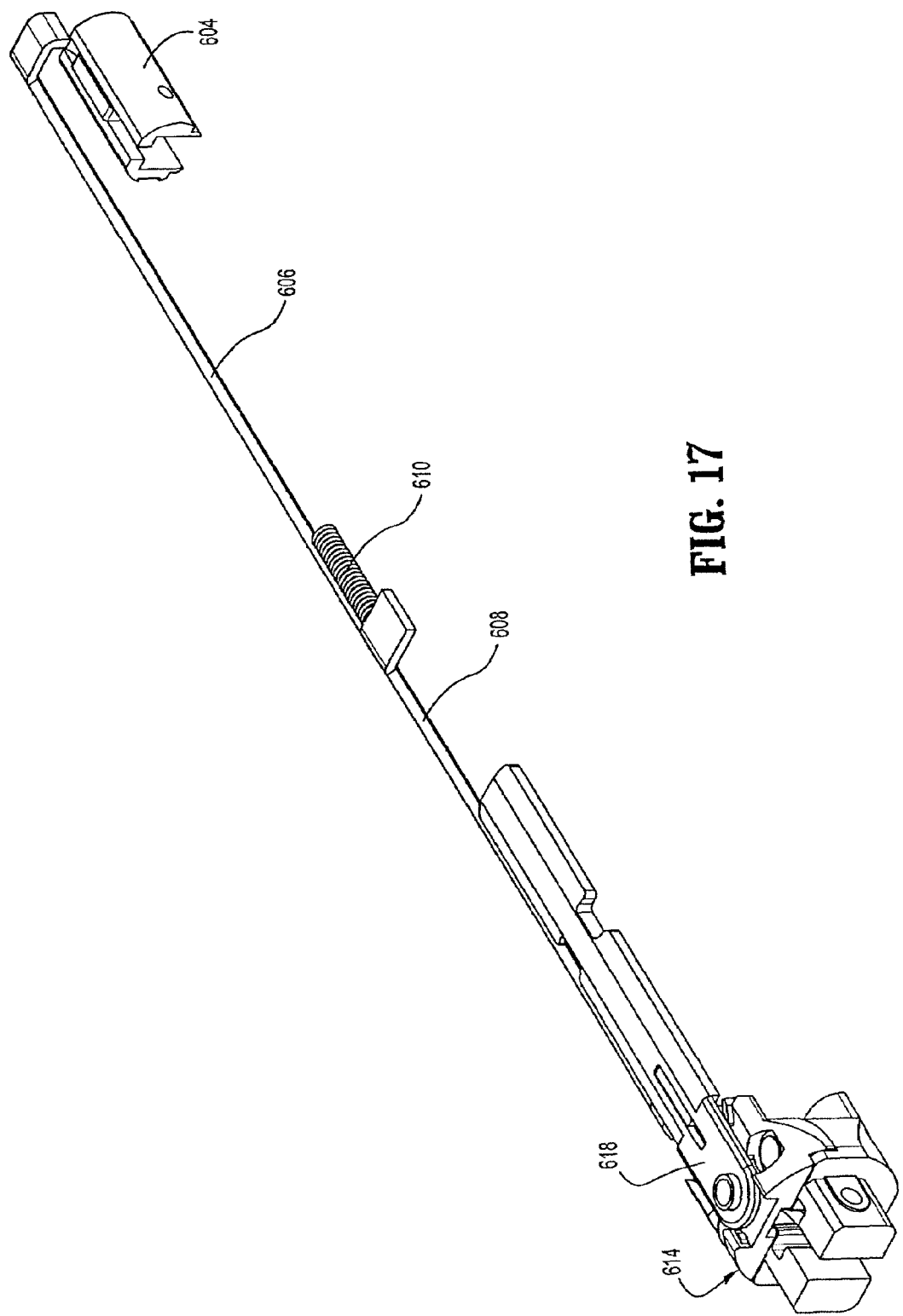
FIG. 17 is a perspective view of various components of the locking assembly of FIG. 16.

Referring to FIGS. 16 and 17, a portion of locking assembly 600 is at least partially contained within a housing 602. FIG. 16 illustrates locking assembly 600 disposed in relation to housing 602, while FIG. 17 illustrates locking assembly 600 isolated from housing 602. In the illustrated embodiment of FIG. 17, pusher 604 is shown with rod 606 extending distally therefrom. Slide 608 extends distally from rod 606 and is in a slidable relationship therewith, thus allowing slide 608 to move axially with respect to rod 606. Spring 610 or pair of springs (not explicitly shown in this embodiment) distally biases slide 608 from rod 606.

Figure 18:
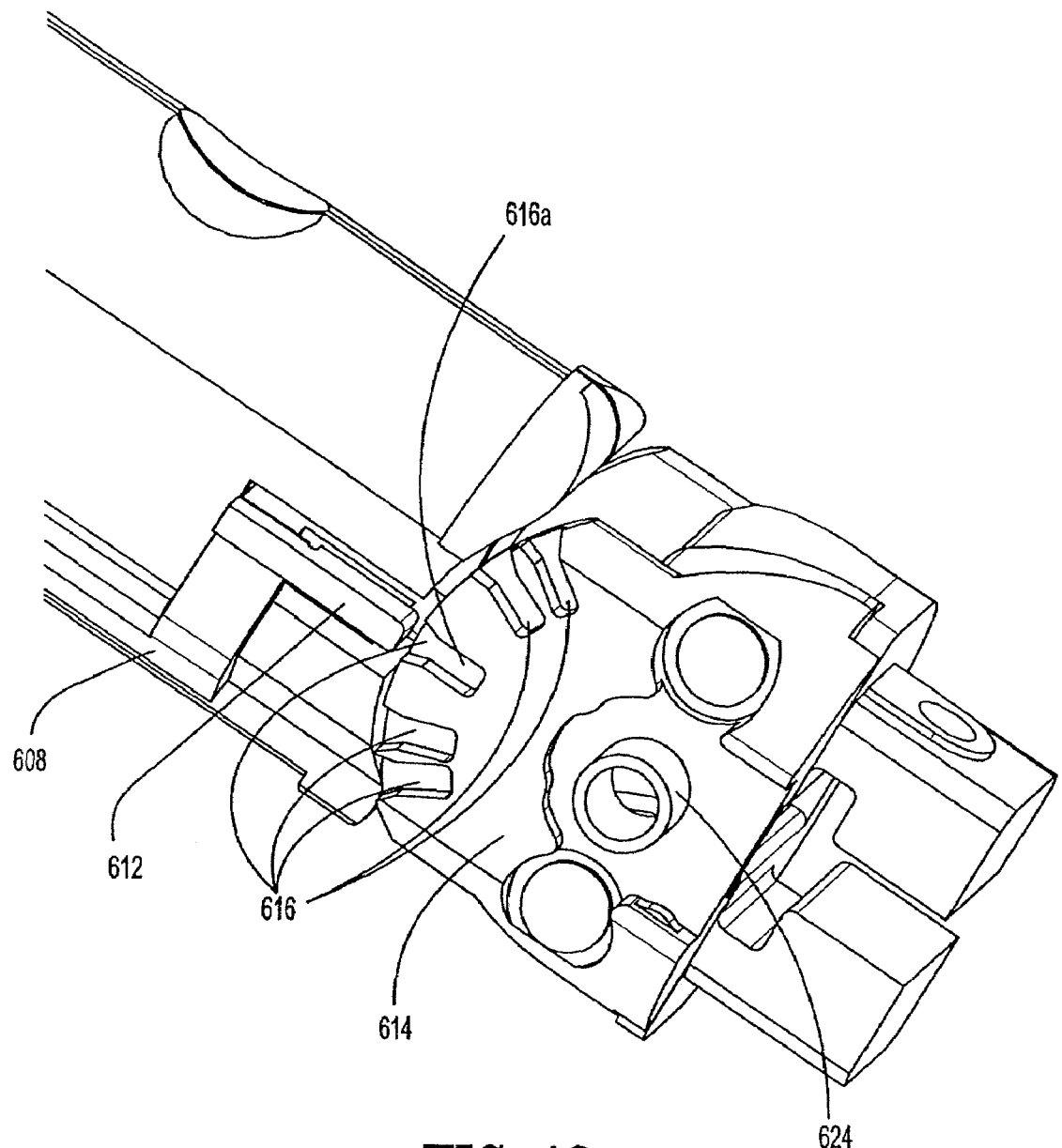
FIG. 18 is an enlarged perspective view of a portion of the locking assembly of FIGS. 16 and 17 illustrated with the articulating tool assembly in a non-articulated position.
Figure 19:
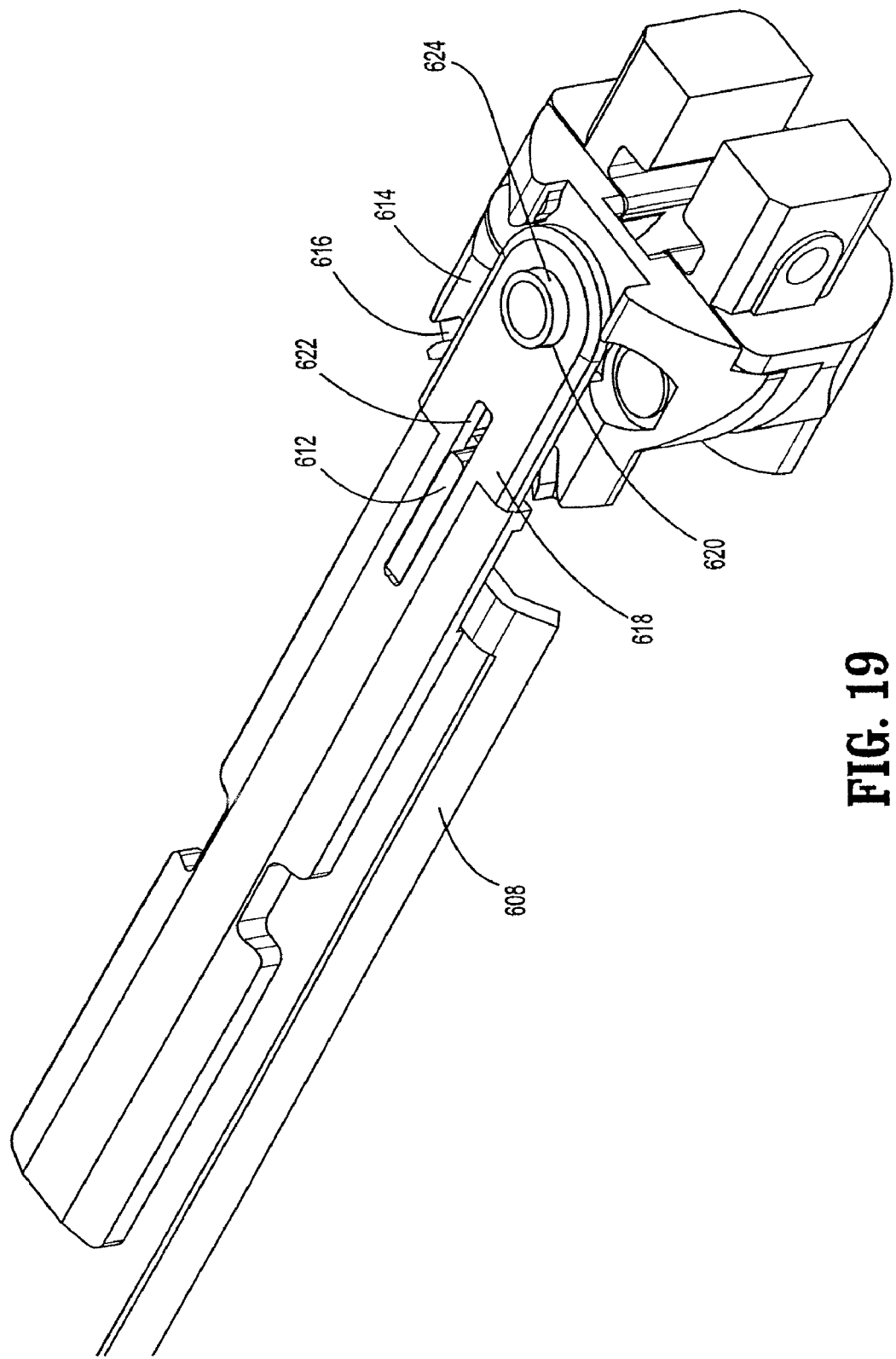
FIG. 19 is an enlarged perspective view of a portion of the locking assembly of FIGS. 16-18 and including a link.
Figure 20:
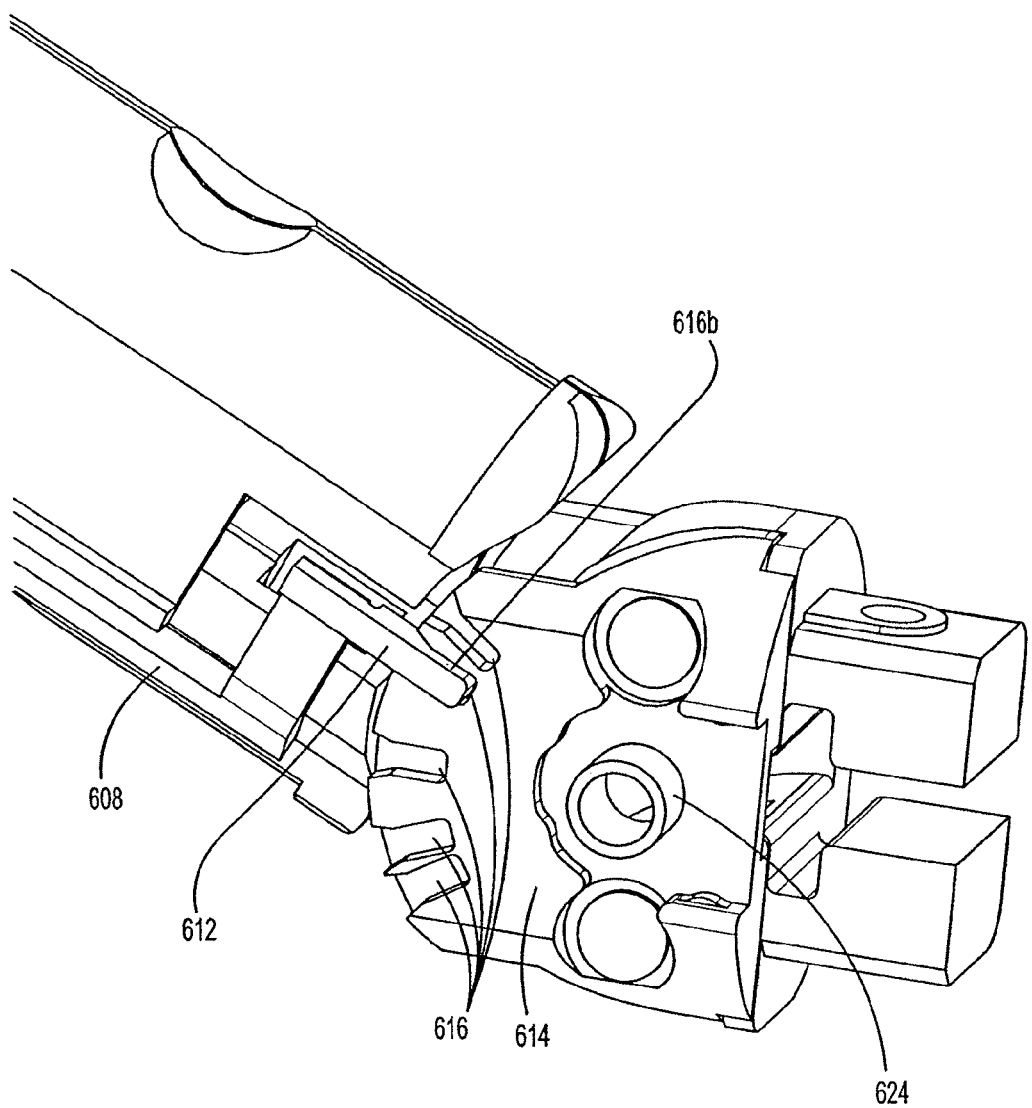
FIG. 20 is an enlarged perspective view of a portion of the locking assembly of FIGS. 16-19 illustrated with the articulating tool assembly in an articulated position.

Now referring to FIGS. 18-20, cam finger 612 and pivot plate 614 are illustrated. Cam finger 612 extends distally from slide 608 and pivot plate 614 may be disposed on mounting assembly 235 (see FIG. 3), for example. It is envisioned that pivot plate 614 may be disposed on or incorporated with a portion of tool assembly 17. A plurality of slots 616 (five slots 616 are illustrated) is disposed on pivot plate 614 and are sized to accept at least a portion of cam finger 612 therein. Upon different amounts of articulation of tool assembly 17 (including no substantial articulation) with respect to body portion 512 (see FIG. 1, for example), cam finger 612 is approximately aligned with an individual slot 616 of pivot plate 614. FIGS. 18 and 19 illustrate cam finger 612 substantially aligned with a center slot 616a (hidden from view in FIG. 19) and FIG. 20 illustrates cam finger 612 substantially aligned with a side slot 616b.

Link 618, illustrated in FIGS. 17 and 19, is in mechanical engagement with pivot plate 614 and cam finger 612. (In FIG. 18, the link has been removed.) Link 618 is illustrated having an opening 620 and a slot 622 (FIG. 19). Opening 620 is in a pivotal relationship with a boss 624 on pivot plate 614 and slot 622 is slidably engaged with cam finger 612. This relationship allows for articulation of pivot plate 614 with respect to body portion 512 and for longitudinal translation of slide 608 with respect to pivot plate 614.

In operation, upon at least a partial actuation of movable handle 516 (see FIG. 1, for example), pusher 604 is forced distally, e.g., via control rod 520 (see FIG. 11, for example), thus causing distal translation of cam finger 612 at least partially into a slot 616 of pivot plate 614. It is envisioned that actuating movable handle 516 to approximate cartridge assembly 18 and an anvil assembly 20 (see FIG. 1A, for example) also functions to translate cam finger 612 distally. In such an embodiment, when articulating tool assembly 17 is in place and clamped on tissue, further articulation cannot be accomplished (without releasing movable handle 516, for example). Thus, locking assembly 600 helps maintain articulating tool assembly 17 in position with respect to body portion 512, prior to emplacing staples into tissue, for example.

As discussed above, spring 610 distally biases slide 608 from rod 606. This biasing provided by spring 610 helps ensure cam finger 612 is not accidentally or prematurely dislodged from slot 616 of pivot plate 614, which may result in a significant amount of "play" therebetween. Additionally, the distal bias provided by spring 610 helps eliminate manufacturing tolerances and/or clearances that are present between slide 608 and pivot plate 614. It is also envisioned that at least a portion of cam finger 612 and/or slot 616 may be wedge-shaped to help reduce any unintended movement therebetween. In such an embodiment, a distal portion of cam finger 612 and slot 616 would be narrower than a corresponding proximal portion.

Figure 21:
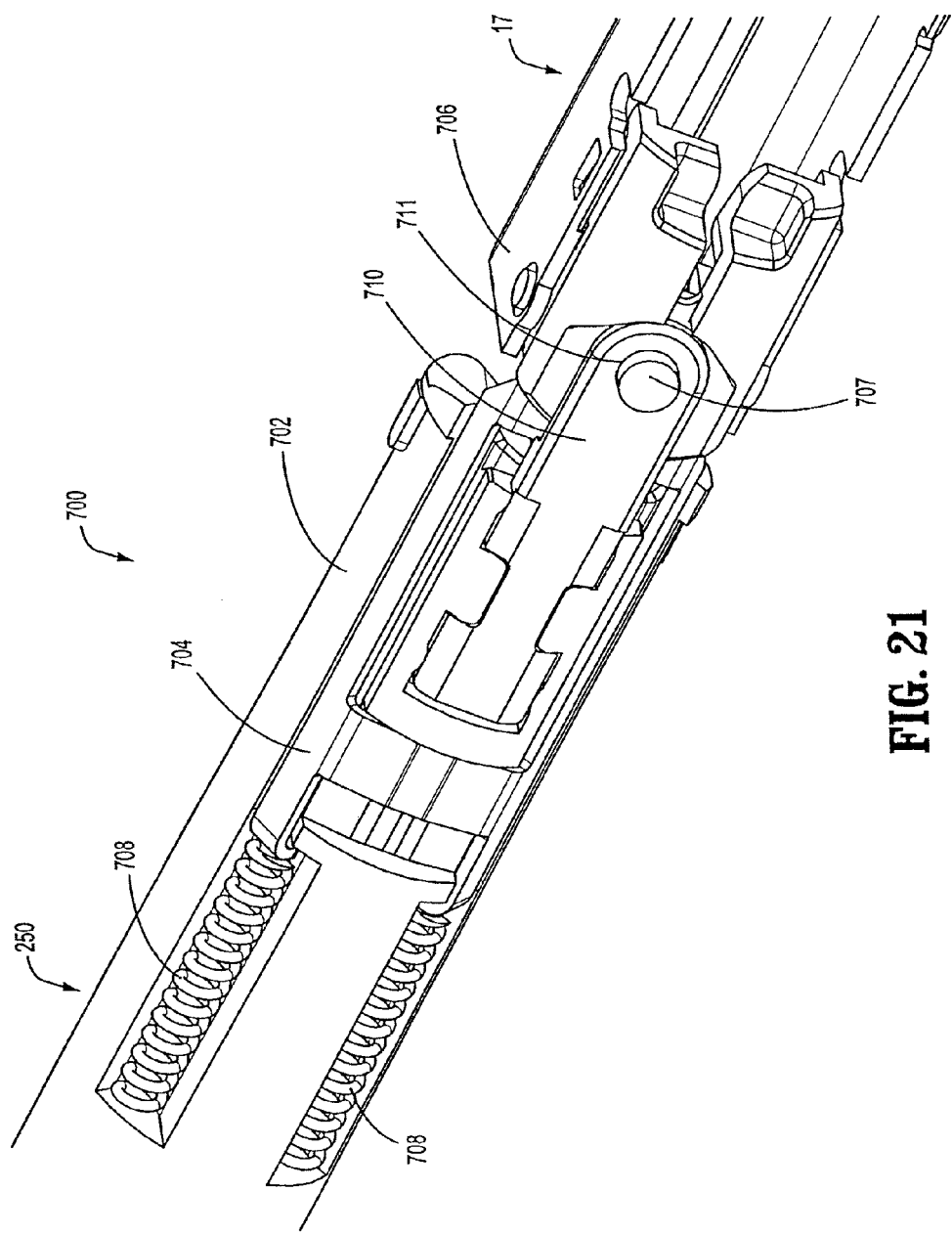
FIG. 21 is an enlarged perspective view of another locking assembly for use with a surgical instrument in accordance with an embodiment of the present disclosure.
Figure 22:
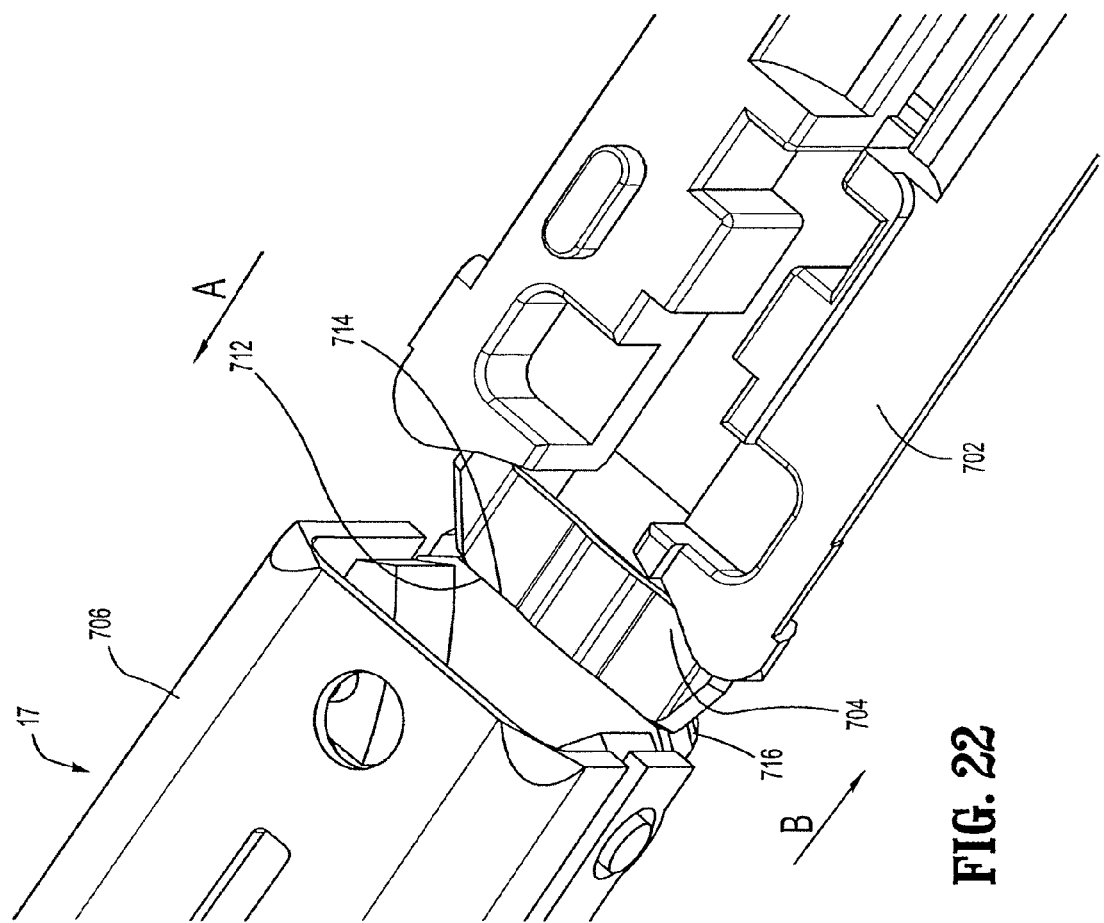
FIG. 22 is an enlarged bottom perspective view of the locking assembly of FIG. 21.

In an embodiment of the present disclosure illustrated in FIGS. 21 and 22, a locking assembly 700 is illustrated for use with surgical instrument 500 and disposable loading unit 16 (see FIG. 1, for example). In the illustrated embodiment, locking assembly 700 includes an adapter 702, a pusher 704, a pivot 706, a biasing element (e.g., a pair of springs 708) and a link 710. Locking assembly 700 generally helps maintain tool assembly 17 in a predetermined position.

With reference to FIG. 21, adapter 702 of locking assembly 700 is generally housed within body portion 512 (see FIG. 1, for example) of surgical instrument 500 or within disposable loading unit 16. In the illustrated embodiment, pusher 704 is located distally of a pair of springs 708. Pusher 704 is distally biased via the pair of springs 708 towards pivot 706 of articulating tool assembly 17. A distal portion of pusher 704 includes a pusher mating surface 712 (FIG. 22) which is shaped and dimensioned to mate with a pivot mating surface 714 (FIG. 22) disposed adjacent a proximal portion of pivot 706. Link 710 is illustrated in mechanical cooperation with a portion of pusher 704 and pivotably connected to a portion of pivot 706, thus allowing articulating tool assembly 17 to move between its first position and its second position with respect to body portion 512. More specifically, link 710 includes an opening 711 that fits over a protrusion 707 of pivot 706, thus allowing pivotal movement therebetween. Further, link 710 is slidably engaged with a portion of adapter 702, thus allowing longitudinal movement therebetween.

Now referring to FIG. 22, pusher mating surface 712 is substantially flat along a majority of its length in this embodiment. Correspondingly, pivot mating surface 714 is also flat along a majority of its length in the illustrated embodiment. Thus, the distal bias of pusher 704 towards pivot 706 (in the direction of arrow A) via the pair of springs 708, helps maintain articulating tool assembly 17 in its first, non-articulated, position, as the biasing force helps articulating tool assembly 17 resist pivoting. While two springs 708 are illustrated, more or fewer springs 708 may be provided.

To pivot articulating tool 17 from its first, non-articulated position, the distal biasing force from pair of springs 708 must be overcome. Such a pivoting action, moves pusher 704 proximally (in the direction of arrow B) against the bias of pair of springs 708. It is also envisioned that pusher mating surface 714 includes detents (not explicitly shown in this embodiment) to help stabilize articulating jaw member 17 in selected articulated positions.

With continued reference to FIG. 22, pivot 706 includes a shelf 716 thereon. As shown in FIG. 22, shelf 716 overlaps at least a portion of pusher 704 when pusher mating surface 712 is in contact with pivot mating surface 714. Shelf 716 is situated and configured to help prevent tissue from being pinched between pusher 704 and pivot 706 when articulating tool assembly 17 is rotated and/or articulated.

Figure 23:
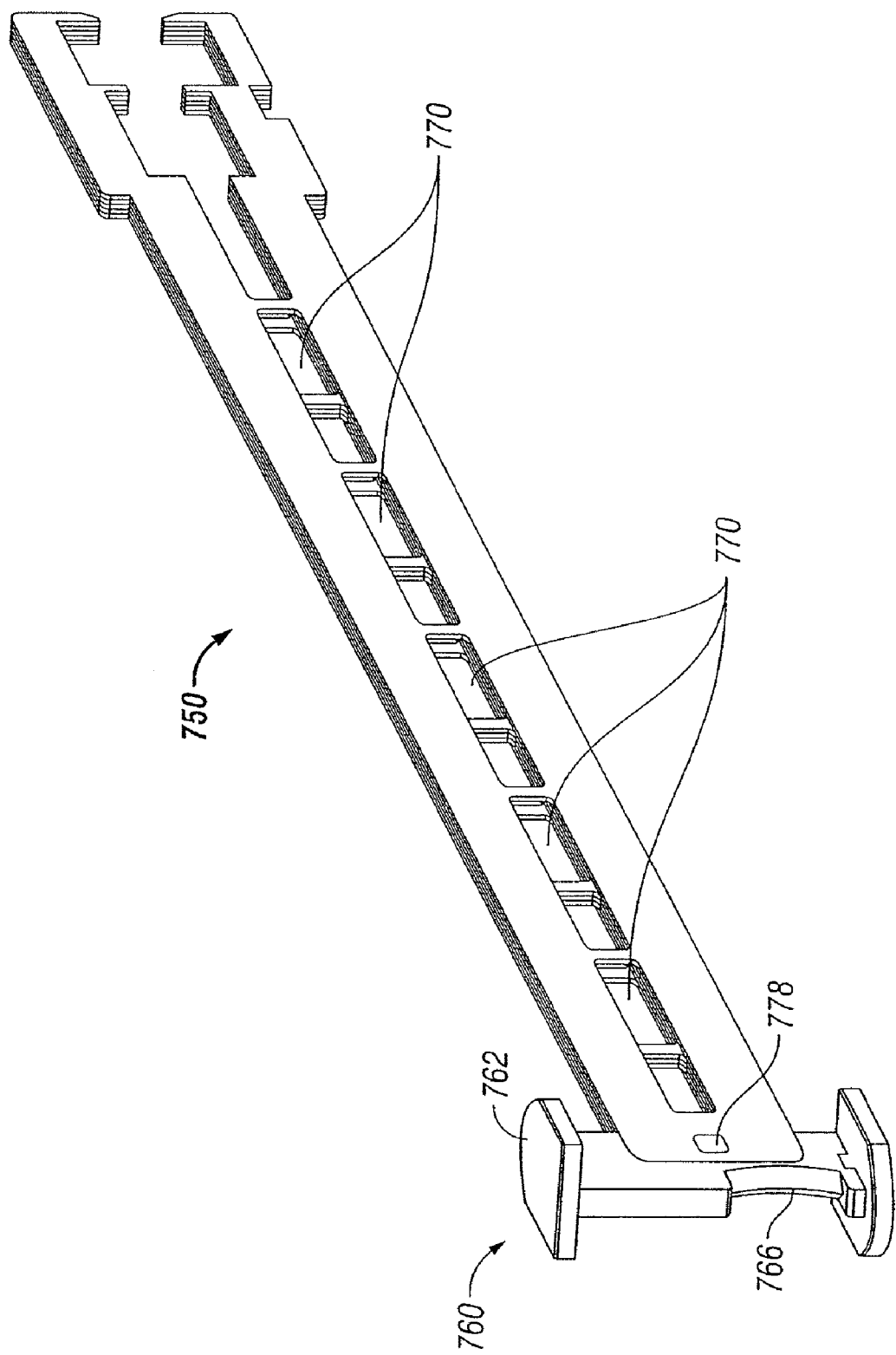
FIG. 23 is a perspective view of a drive beam having a plurality of layers and a closure apparatus in accordance with an embodiment of the present disclosure.
Figure 24:
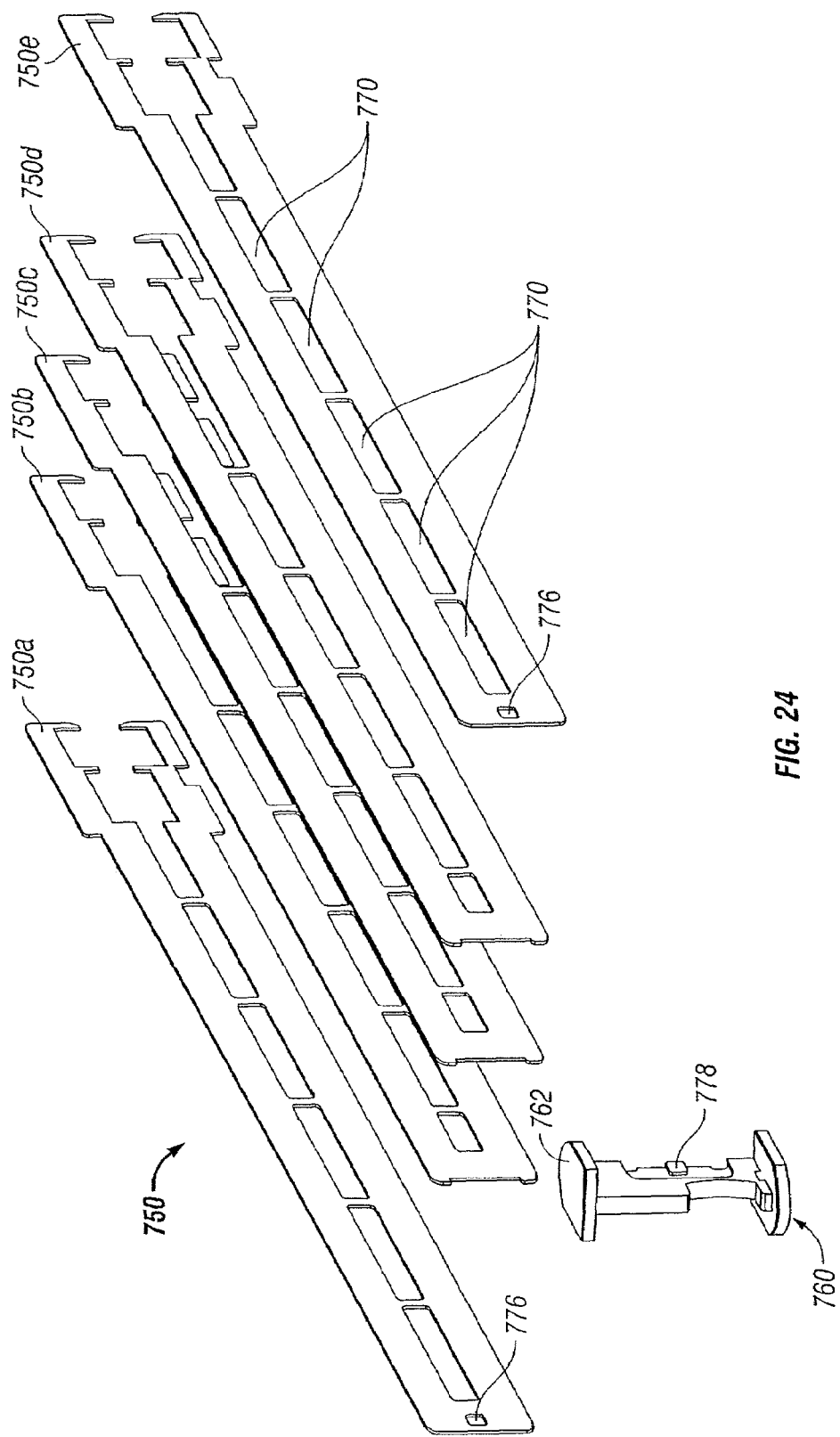
FIG. 24 is a perspective view of the drive beam and closure apparatus of FIG. 23 with parts separated.
Figure 25:
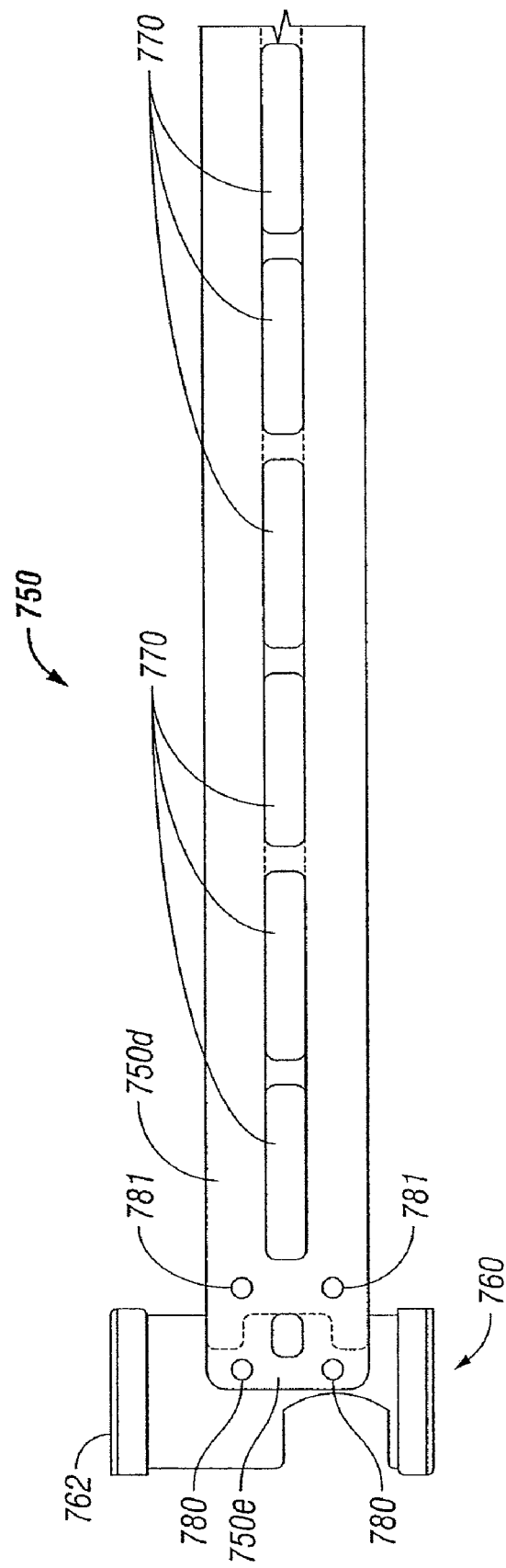
FIG. 25 is a cross-sectional view of a portion of the drive beam and closure apparatus of FIGS. 23 and 24.

In an embodiment of the present disclosure illustrated in FIGS. 23-25, a multi-layered drive beam 750 having a plurality of layers 750a-750e is illustrated and may be included in a disposable loading unit 16 (see FIG. 1, for example). A closure apparatus 760, such as an I-beam, is also illustrated. Closure apparatus 760 includes a horizontal portion 762 that is advanceable into camming surface 42 (or other contact surface) to approximate tool assembly tool assembly 17, as described in detail above with reference to FIG. 2.

With reference to FIG. 24, multi-layered drive beam 750 having five layers 750a-750e is illustrated. It is envisioned and within the scope of the present disclosure that fewer or more layers may be used to form multi-layered drive beam 750. It is also envisioned that multi-layered drive beam 750 may replace drive beam 266 in other embodiments of this disclosure. Use of multi-layered drive beam 750 may provide increased strength and flexibility during use, specifically, for instance, while tool assembly 17 is in an articulated position.

A plurality of cutouts 770 is illustrated in FIGS. 23-25 which extend through each layer of multi-layered drive beam 750. Although the figures show between five and ten cutouts per layer of multi-layered drive beam 750, the exact number of cutouts 770 may be fewer than five, between five and ten, or greater than ten. Additionally, cutouts 770 of adjacent layers of drive beam 750 may or not align with each other. The use of cutouts 770 reduces cross-sectional dimensions of drive beam 750 and allows for bending force adjustment. While rectangular cutouts 770 are illustrated, the use of cutouts 770 having other regular or non-regular shapes is also contemplated.

The attachment of each layer 750a-750e of multi-layered drive beam 750 and the attachment to closure apparatus 760 are illustrated in FIG. 25. In the illustrated embodiment, an outer layer (750a or 750e of FIG. 24) is affixed to closure apparatus 760 in two locations (each location being indicated by numeral 780 in FIG. 25), via a pair of spot welds, for example. It is also envisioned that each outer layer 750a, 750e includes an aperture 776 that fits over a boss 778 protruding from closure apparatus 760. Each outer layer 750a, 750e is also affixed to an adjacent layer (e.g., 750b or 750d) in two locations (each location being indicated by numeral 781 in FIG. 25), possibly via a pair of spot welds. Further, each inner layer (e.g., 750b, 750c and 750d) is attached to an adjacent inner layer (for instance, 750b is attached to 750c; 750c is attached to 750b and 750d; and 750d is attached to 750c) in two locations, via spot welds, for example. While spot welding is disclosed as an attachment method, other methods for attaching each layer to each other and the outer layers to the closure apparatus are envisioned and within the scope of the present disclosure. The illustrated embodiments show attachments points 780 of inner layers adjacent closure apparatus 760, but it is envisioned and within the scope of the present disclosure that attachment points 780 are disposed in other locations on drive beam 750. Additionally, it is envisioned that at least one layer of drive beam 750 is made of a metal, such as stainless steel. Portions of drive beam 750 and/or closure apparatus 760 may also be made of or at least partially coated with a plastic material, as described below. Further, closure apparatus 790 may include a cutting surface 766 (FIG. 23) thereon for cutting tissue.

Figure 26:
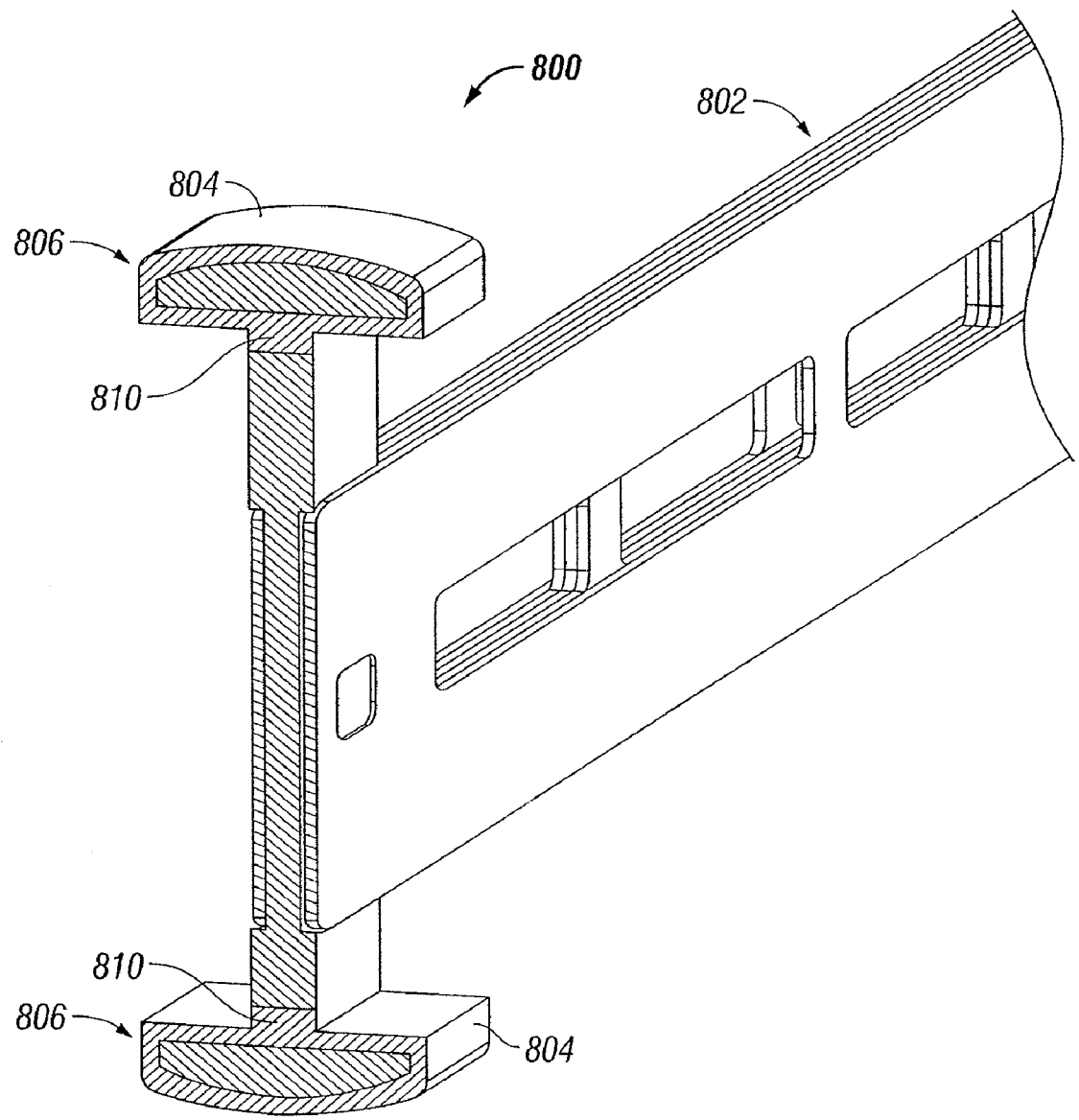
FIG. 26 is a cross-sectional view of a drive beam and a closure apparatus in accordance with an embodiment of the present disclosure.
Figure 27:
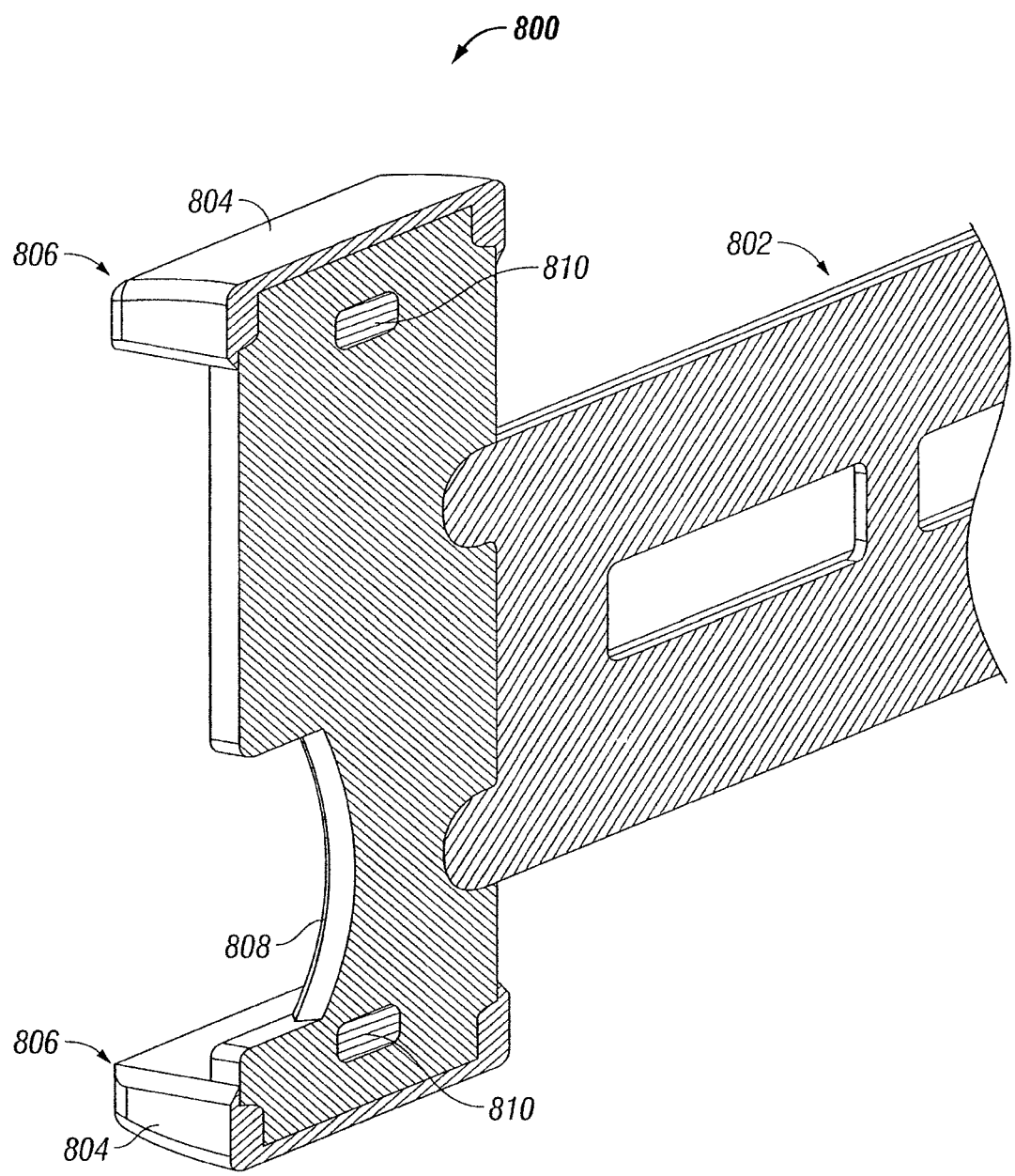
FIG. 27 is a cross-sectional view of the drive beam and closure apparatus of FIG. 26.
Figure 28:
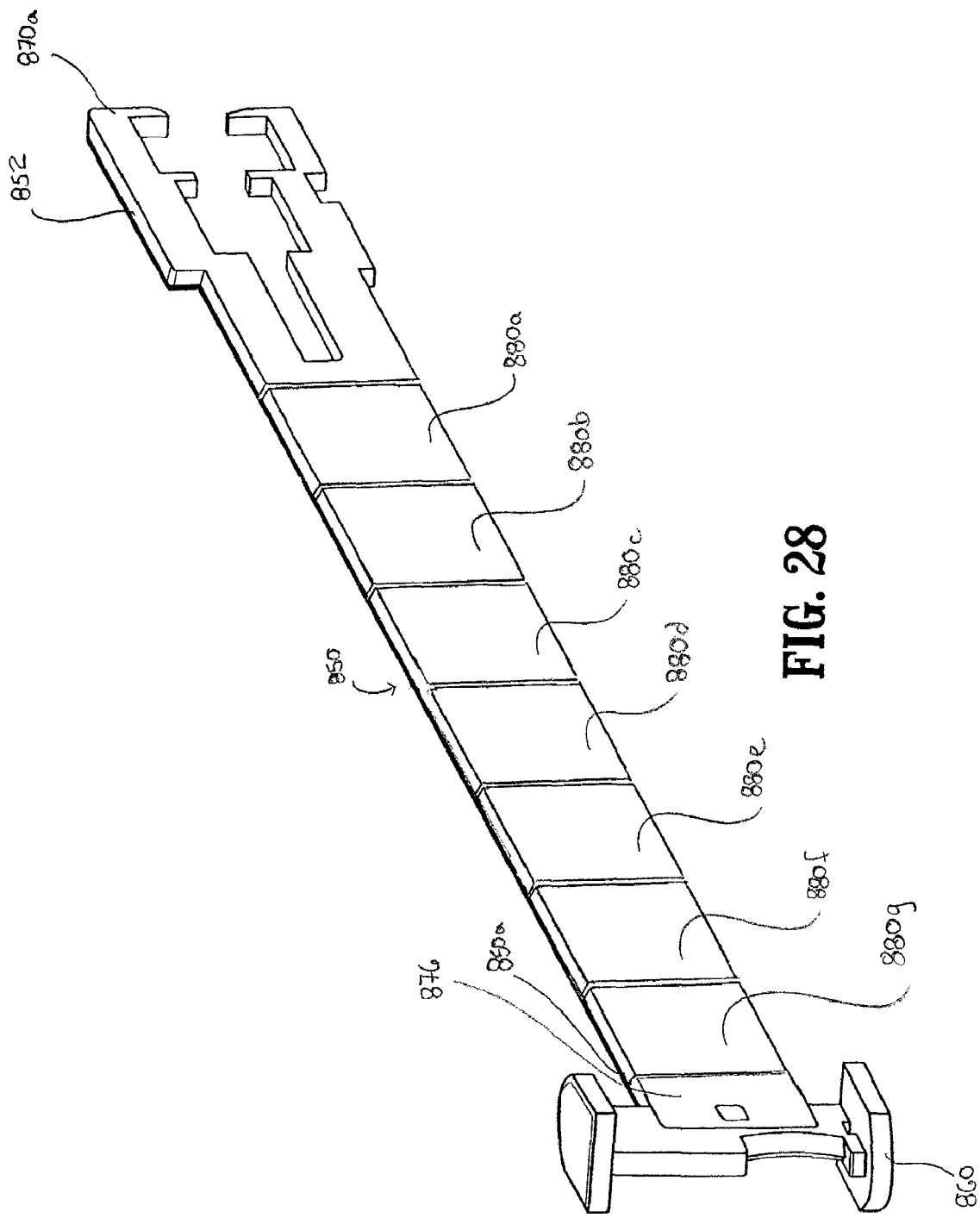
FIG. 28 is a perspective view of a drive beam according to an alternate embodiment of the present disclosure including a single flexible band and multiple segments or pads and a closure apparatus.

In an embodiment of the present disclosure illustrated in FIGS. 26 and 27, a closure apparatus 800 and a portion of drive beam 802 are shown. Closure apparatus and/or a contact surface (e.g., camming surface 42) of tool assembly 17 (see FIG. 2, for example) may include a plastic surface or plastic coating. In this embodiment, closure apparatus 800 is illustrated having a pair of caps 804 at least partially covering horizontal portions 806 of closure apparatus 800. Caps 804 may be made of plastic in this embodiment. Such plastic surfaces disposed on closure apparatus 800 and/or contact surface of tool assembly 17 generally reduce the amount of friction therebetween vis-à-vis two metal surfaces. That is, a plastic to metal or a plastic to plastic interaction creates less friction than interaction between a pair of metal surfaces. Reducing the friction during movement of closure apparatus 800 reduces the firing force required to operate surgical instrument 500. The reduction in the amount of friction between surfaces is particularly beneficial during longitudinal translation of closure apparatus 800.

It is envisioned that a portion of closure apparatus 800, such as pair of caps 804, is made of plastic, overmolded with plastic or includes a plastic coating. Additionally, a contact surface of tool assembly 17, or at least a portion thereof, may also be made of plastic, be overmolded with plastic or include a plastic coating.

In an embodiment of the disclosure, closure apparatus 800 may include an I-shaped cross section, as illustrated in FIGS. 26 and 27. Additionally, closure apparatus 800 and drive beam 802 may be part of a disposable loading unit 16 and/or part of a surgical instrument 500 that is able to articulate. Further, drive beam 802 may include a single layer or a plurality of layers (as shown in FIG. 26) and at least a portion of drive beam 802 may be made of plastic. Still further, closure apparatus 800 may include a cutting surface 808 (FIG. 27) thereon for cutting tissue.

With continued reference to FIGS. 26 and 27, plastic cap 804 may include a reinforced section 810, composed of a stronger or more durable material, which may increase the strength of closure apparatus 800 or may provide a stronger connection between cap 804 and horizontal portion 806 of closure apparatus 800. It is also envisioned that cap 804 may be removably attached to closure apparatus 800. In such an embodiment, cap 804 may be removed and replaced if any substantial wearing or damage occurs.

An alternate embodiment of drive beam of the present disclosure illustrated in FIGS. 28-34B and is shown generally as segmented drive beam 850. Segmented drive beam 850 includes a flexible band 852 and a plurality of pads or segments 880a-880g securely mounted thereto. Segmented drive beam 850 may be configured for use in disposable loading unit 16, disclosed above. Segmented drive beam 850 may further include a closure apparatus 860, such as an I-beam, as shown. Closure apparatus 860 is substantially similar to closure apparatus 760, as described in detail above with reference to FIGS. 26 and 27.

With continued reference to FIGS. 28-34B, segmented drive beam 850 includes flexible band 852 of single layer and multiple segments 880a-880g. It is envisioned and within the scope of the present disclosure that a plurality of layers may be used to form flexible band 852. Additionally, any number of segments 880 may be used to form segmented drive beam 850. It is further envisioned that segmented drive beam 850 may replace drive beams 266, 750 in the other embodiments of this disclosure, as well as in other surgical instruments employing a drive beam. Use of segmented drive beam 850 may provide increased strength and flexibility during use, specifically, for instance, while tool assembly 17 is in an articulated position.

Figure 30:
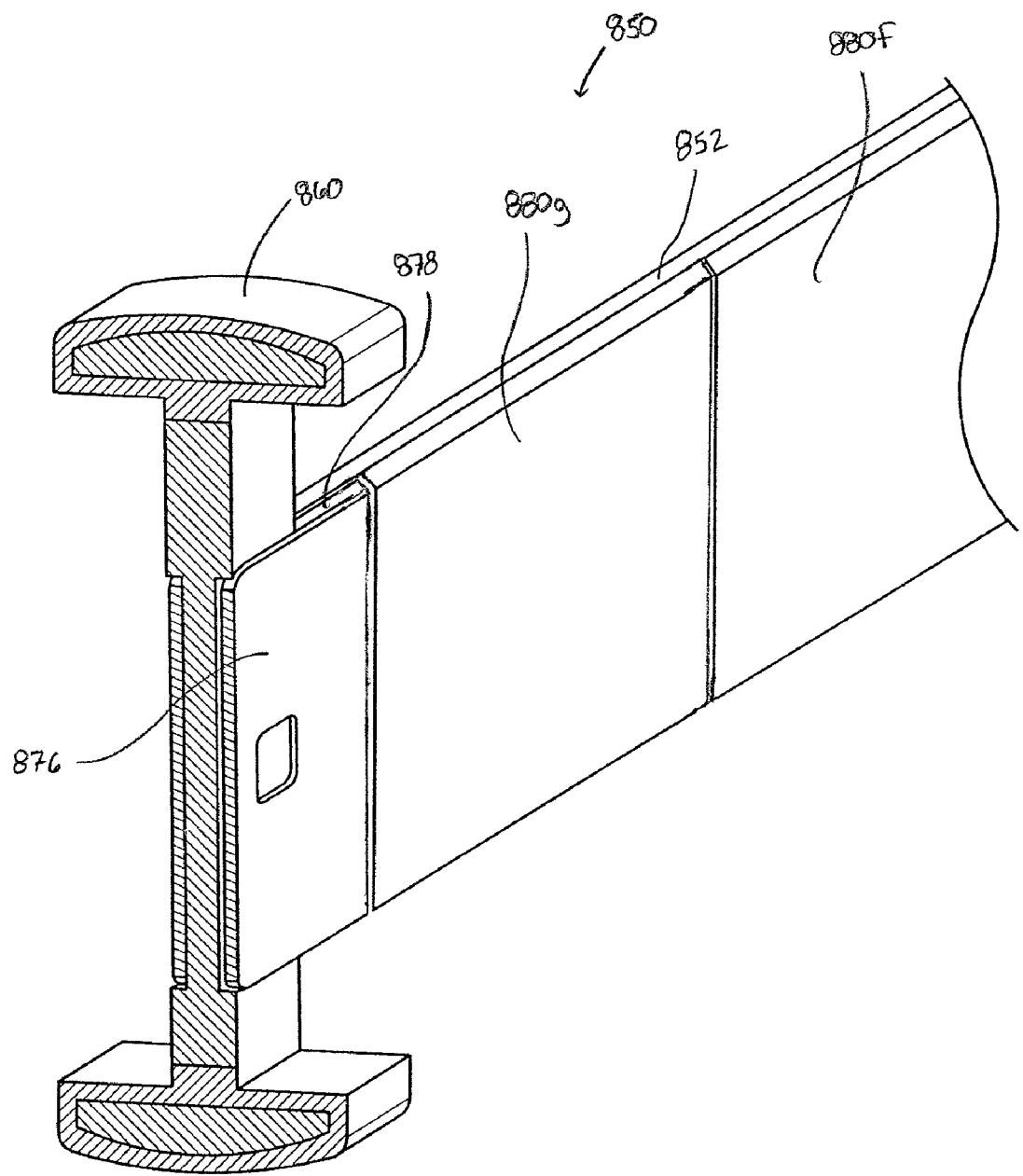
FIG. 30 is a cross-sectional view of a portion of the drive beam and closure apparatus of FIGS. 28 and 29.
Figure 31:
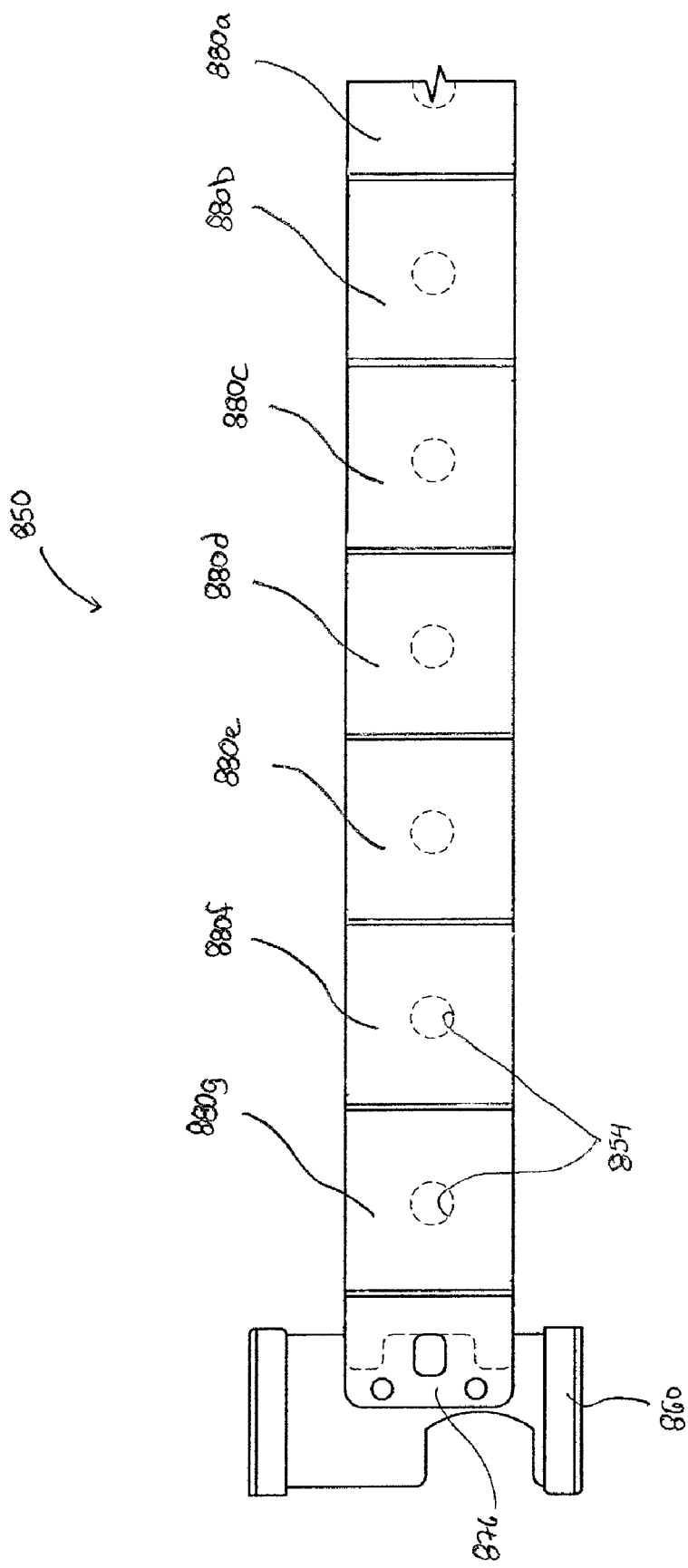
FIG. 31 is a side view of the drive beam and closure apparatus of FIG. 30.
Figure 32A:
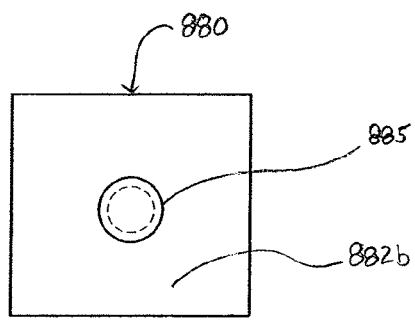
FIG. 32A-D are various views of a representative segment of the drive beam of FIGS. 28-31.
Figure 32B:
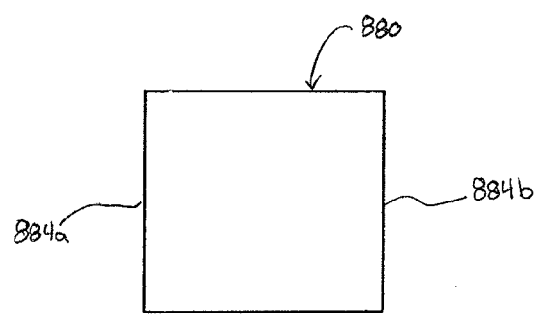
Figure 32C:
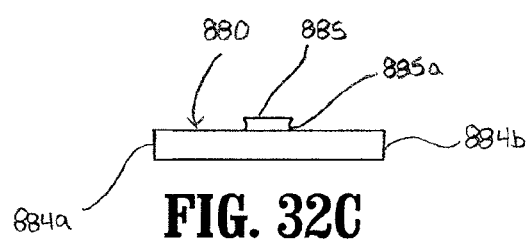
Figure 32D:
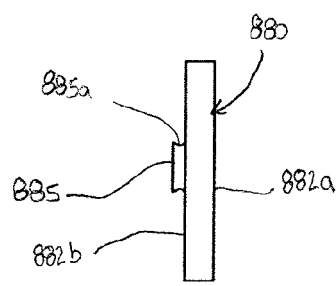
Figure 34:
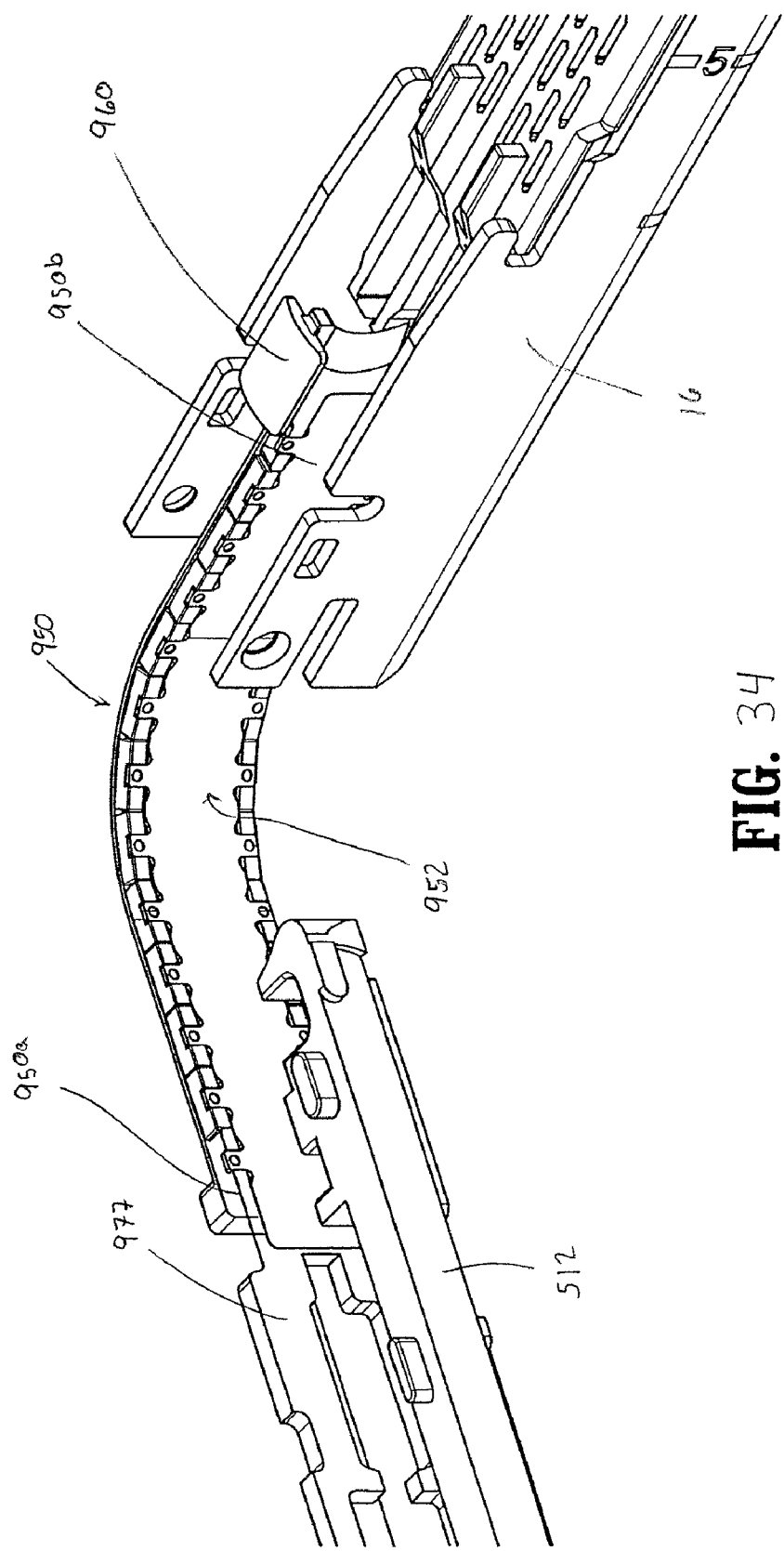
FIG. 34 is a side perspective view of a drive beam according to an another embodiment of the present disclosure.
Figure 35:
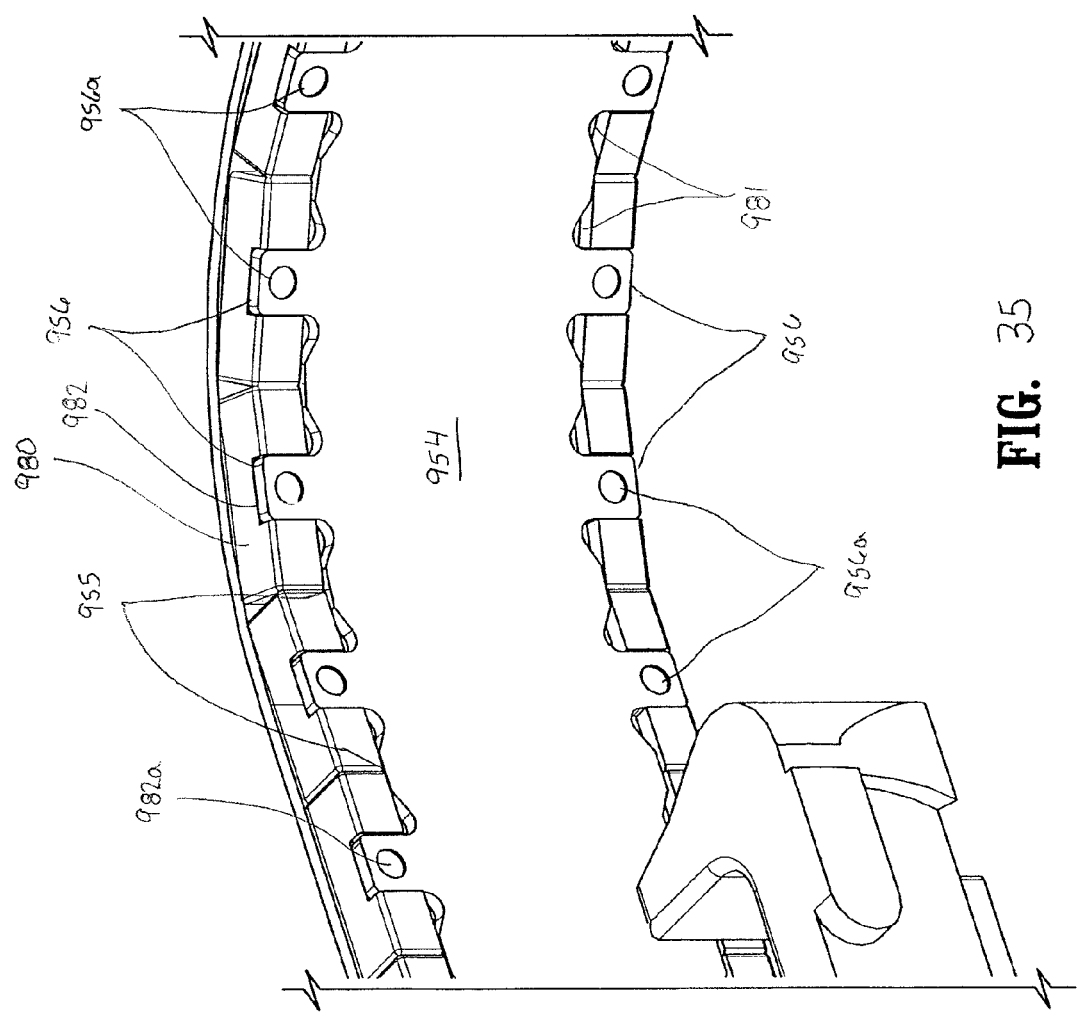
FIG. 35 is an enlarged side view of the drive beam of FIG. 34.
Figure 36:
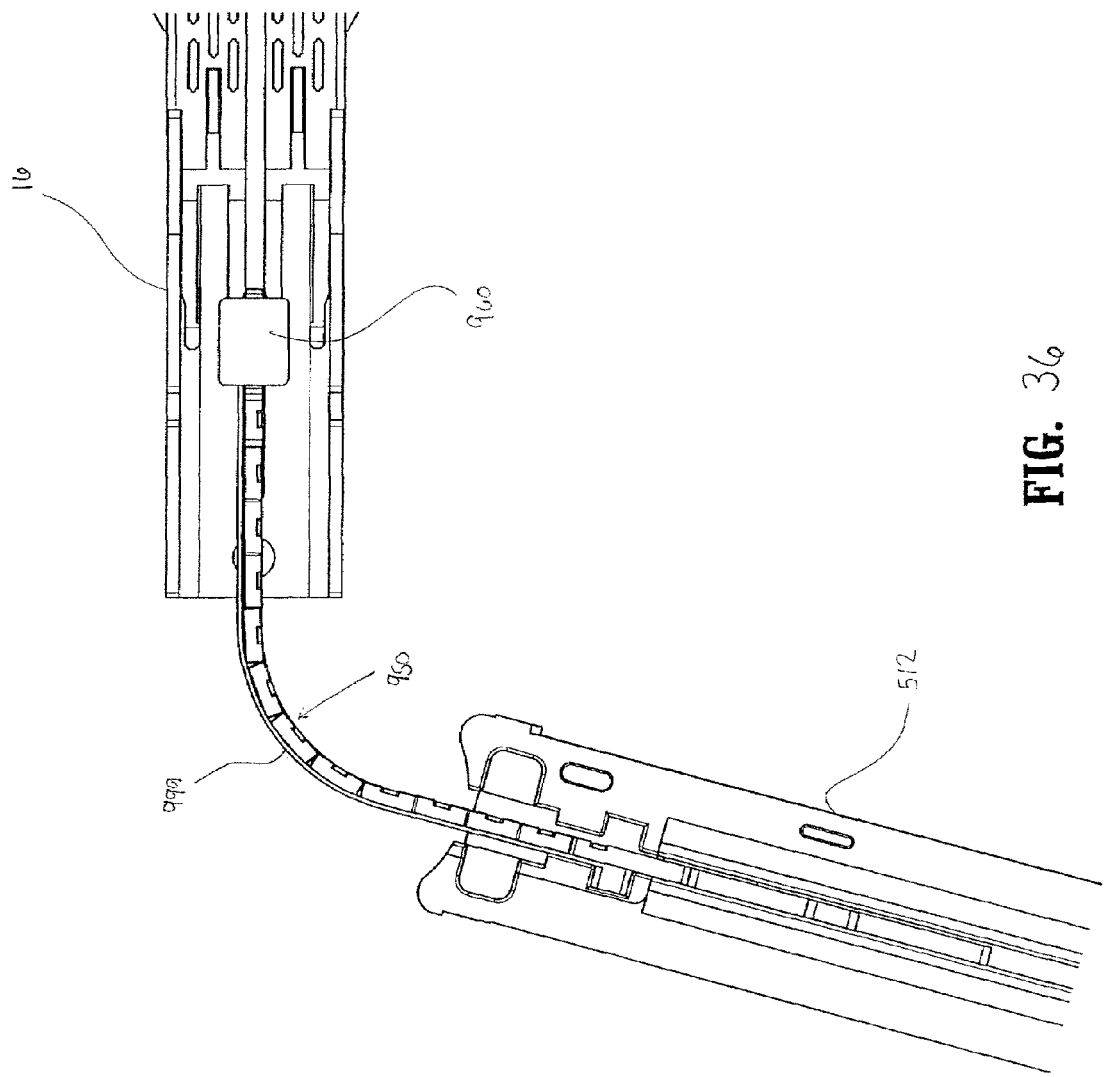
FIG. 36 is a top view of the drive beam of FIGS. 34 and 35.
Figure 37:
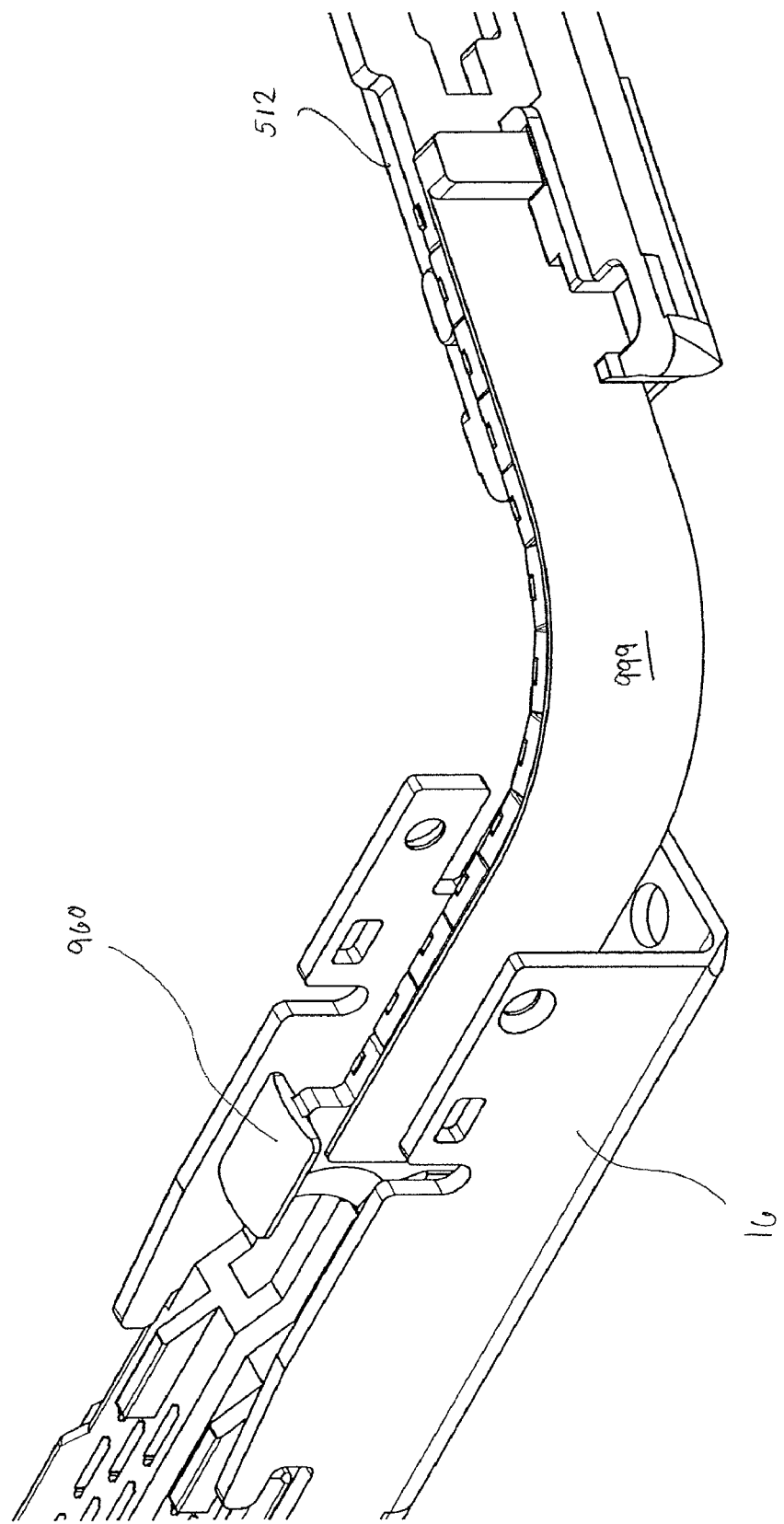
FIG. 37 is an opposite side view of the drive beam of FIGS. 34-37.

Referring initially to FIG. 30, flexible band 852 is substantially similar to flexible bands 750a-e described above and will only be described in detail as relates to the differences therebetween. Flexible band 852 may be formed of a single layer, as shown, or may instead include multiple layers. When that multiple flexible bands 852 are employed, the bands may be joined in a manner as described above with reference to flexible bands 750a-e. Flexible band 852 defines openings 854 for securely receiving segments 880, as will be described in further detail below. As with flexible bands 750a-e, proximal and distal ends 852a, 852b of flexible band 852 are configured for operable engagement with a drive assembly and a tool assembly, respectively.

Figure 29:
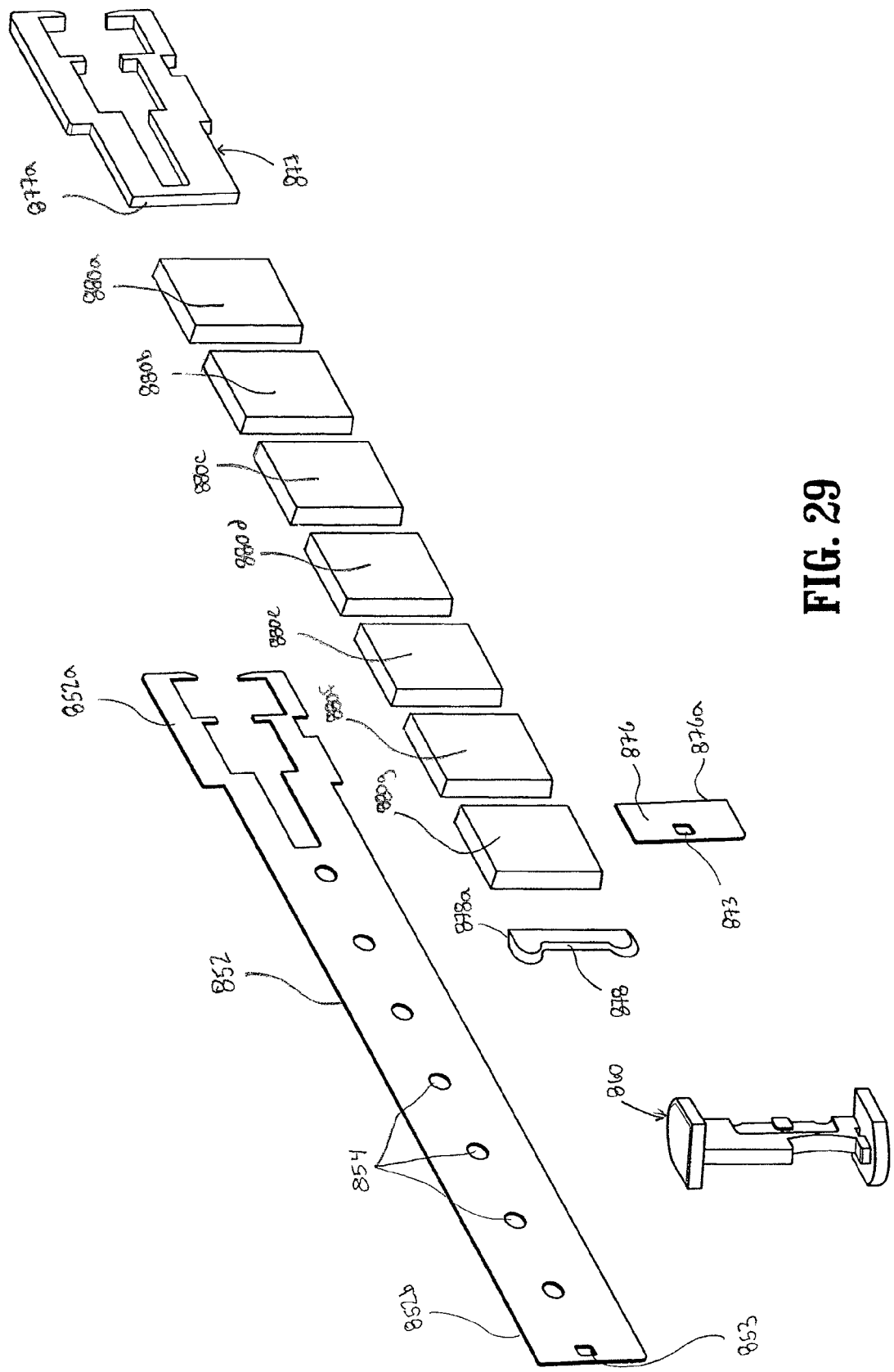
FIG. 29 is a perspective view of the drive beam and closure apparatus of FIG. 28 with parts separated.

Proximal end 850a (FIG. 28) of segmented drive beam 850 includes a connecting member 877 (FIG. 29). Connecting member 877 is configured be secured to proximal end 852a of flexible band 852. Connecting member 877 may be constructed of metal, plastic, or the like. Connecting member 877 may be secured to flexible band 852 in any known manner, including but not limited to, with adhesive, spot welding, mechanical fasteners and the like. Together, connecting member 877 and proximal end 852a of flexible band 852 are configured to operably connect proximal end 850a of segmented drive beam 850 with control rod 520 (FIG. 12). Connecting member 877 defines a leading edge 877a. Leading edge 877a of connecting member 877 may be configured to operably engage a trailing edge of proximal most segment 880a.

Distal end 850b of segmented drive beam 850 is configured for operable engagement with closure apparatus 860. Distal end 850b includes distal end 852b of flexible band 852 and a bracket 876 configured to cooperate with distal end 852b to operably connect segmented drive beam 850 with closure apparatus 860. Distal end 850b may also include a spacer 878 positioned between distal end 852b of flexible band 852 and bracket 876. Distal end 852b of flexible band 852 and bracket 876 define corresponding openings 853, 873, respectively, for operably connecting segmented drive beam 850 with closure apparatus 860. Spacer 878 and bracket 876 may be connected to distal end 852b of flexible band 852, and to each other, in any known manner, including with adhesive, mechanical fasteners, welding and the like. Bracket 876 and spacer 878 each include trailing edges 876a, 878a. Trailing edges 876a, 878a may be configured to operably engage a trailing edge of distal most segment 880g. As will be discussed below as relates to segments 880a-g, leading edges 876a, 878a are formed at a right angle relative to flexible band 852. In other embodiments of the present disclosure, the bracket 876 and/or spacer 878 are omitted.

With particular reference now to FIGS. 32A-D, a representative illustration of segments 880a-880g is shown as segment 880. Segment 880 forms a substantially planar member having front and back surfaces 882a, 882b, respectively, and leading and trailing edges 884a, 884b, respectively. Segment 880 may be formed from metal, plastic, or the like. Extending from back surface 882b of segment 880 is a mounting member or connector 885. Mounting member 885 is configured for joining segment 880 to flexible band 852. Mounting member 885 may be integrally formed with segment 880. Mounting member 885 may define a groove or recess 885a for securing segment 880 with openings 854 formed in flexible band 852 (FIG. 29). Alternatively, segment 880 may include a tab, slot, threaded opening or the like, for affixing segment 880 to flexible band 852.

With reference to FIGS. 33A and 33B, the operation of segmented drive beam 850 will now be described. Segmented drive beam 850 is operably received between body portion 512 and loading unit 16 of surgical instrument 500 (FIG. 1). A blowout plate 899 is positioned adjacent to segmented drive beam 850 and extends between body portion 512 and loading unit 16. As will be discussed in further detail below, blowout plate 899 is configured to prevent segment drive beam 850 from buckling during activation of surgical instrument 500.

Referring initially to FIG. 33A, in a first, non-articulated position, a firing force "F" is applied to a proximal end 850a of segmented drive beam 850. Firing force "F" is transferred longitudinally along segmented drive beam 850 predominately through segments 880, as represented by dashed line "F1". Firing force "F" is sufficient to overcome the value resistance "R" in disposable loading unit 16, thereby causing the longitudinal advancement of closure apparatus 860. Blowout plate 899 inhibits buckling of segmented drive beam 850 in a first direction (to the left in FIG. 33A) and flexible band 852 inhibits buckling in a second direction (to the right).

Turning now to FIG. 33B, the segmented configuration of segmented drive beam 850 permits disposable loading unit 16 of surgical instrument 500 (FIG. 1) to articulate relative to body portion 512. Firing force "F" is again applied to segmented drive beam 850 to overcome resistance "R" and again firing force "F" is transferred through segments 880, as represented by dashed line "F2". Blowout plate 899 again inhibits buckling in a first direction and flexible band 852 inhibits buckling in the opposite direction. The configuration of segmented drive beam 850 permits disposable loading unit 16 to be articulated up to ninety degrees (90°) relative to body portion 512 of surgical instrument 500.

In certain embodiments, the segments 880 include angled surfaces. The leading edge 881a of a first segment 881 has a first surface 880a and a second surface 880b and the second surface is angled with respect to the first surface. The trailing edge 883a of a second segment 883 has a first surface 880c and a second surface 880d and the second surface is angled with respect to the first surface. The leading edge 881a has a shape that is complementary to the shape of the trailing edge 883a and each of these edges define a point 885a and 885b. During articulation shown in FIG. 33B, the first segment 881 and second segment 883 rotate with respect to one another, about points 885a and 885b, flexing the band. The load is transferred at surfaces 880b and 880c.

Referring now to FIGS. 34-37, a segmented drive beam according to an alternate embodiment of the present disclosure is shown generally as segmented drive beam 950. Segmented drive beam 950 includes a connecting member 977, a flexible band 952, a plurality of segments 980, and a closure apparatus 960. Closure apparatus 960 and connecting member 977 are substantially similar in form and function to closure apparatus 860 and connecting member 877 described hereinabove. Connecting member 977 is operably connects proximal end 950a of segmented drive beam 950 with an axial drive assembly (not shown) of a surgical stapling device (not shown) and closure apparatus 960 operably connects distal end 950b with a tool assembly (not shown) of the surgical stapling device.

Flexible band 952 includes a substantially planar body portion 954 and a plurality of opposed flanges 956 outwardly extending along the length of body portion 954. Body portion 954 includes segment contacting surfaces 955 extending between flanges 956. Segment contacting surfaces 955 span between adjacent segments 980 and are configured to reinforce segments 980 as segmented drive beam 950 is articulated and longitudinally advanced. As will be discussed in further detail below, each of flanges 956 include an opening 956a for receiving a tab 982a formed on segments 980. Flexible band 952 may be composed of plastic, metal, polymer or their suitable material. A proximal end 952a of flexible band 952 is configured for operable engagement with connecting member 977. A distal end 952b of flexible band 952 is configured for operable engagement with closure apparatus 960.

Still referring to FIGS. 34-37, segments 980 are configured to be engaged by flexible band 952. Each of segments 980 include a first recess 981 and a pair of laterally extending second recesses 982. First recess 981 is configured to receive body portion 954 of flexible band 952. Each of second recesses 982 is configured to receive flange 956 of flexible band 952. Each of second recesses 982 include tab 982a configured to engage openings 956a formed on flanges 956. Segments 980 may be spot-welded, adhered or otherwise suitably fastened to flanges 956 of flexible band 952, with or without the use of tabs 982a.

Segmented drive beam 950 operates substantially similar to segmented drive beam 850 described hereinabove. Segmented drive beam 950 is operably received between a body portion 512 and disposable loading unit 16 of surgical instrument 500 (FIG. 1). A blowout plate 999 prevents buckling of segmented drive beam 950 in a first direction and flexible band 852 prevents buckling in a second, opposite direction.

It will be understood that various modifications may be made to the embodiments disclosed herein. For example, the above-described segmented drive beam may include segments attached to a first and a second surface of a flexible band. In this manner, in either the axially aligned or articulated positions, an axial force provided to the segmented drive beam would be transferred along the flexible band, as well as along of the set of segments. Further, flexible band and any or all of segments may be integrally formed. Therefore, the above description should not be construed as limiting, but merely as exemplifications of various embodiments. Those skilled in the art will envision other modifications within the scope and spirit of the claims appended hereto.

What is claimed is:

1. A surgical instrument, comprising:
   a handle portion;
   an elongated body portion extending distally from the handle portion and defining a longitudinal axis;
   a tool assembly mounted on a distal end of the body portion, the tool assembly being articulatable from a first position substantially aligned with the longitudinal axis to a second position; and
   a drive member operably connecting the handle portion to the tool assembly and configured for actuating the tool assembly in at least the first and second position, the drive member including a flexible band having a first surface and a second surface, and a plurality of substantially planar segments mounted along the first surface of the flexible band.

2. The surgical instrument according to claim 1, wherein each of the plurality of segments includes a leading edge and a trailing edge.

3. The surgical instrument according to claim 2, wherein the leading edge of a first segment is in contact with the trailing edge of a second segment when the tool assembly is in one of the first or second position.

4. The surgical instrument according to claim 1, wherein a plurality of segments is mounted on the second surface of the band.

5. The surgical instrument according to claim 1, wherein the plurality of segments is mounted on the first surface of the band and further comprising a plate disposed adjacent the second surface of the band.

6. The surgical instrument according to claim 1, wherein the band has multiple layers.

7. The surgical instrument according to claim 1, wherein at least one of the plurality of segments includes an angled surface.

8. The surgical instrument according to claim 7, wherein a first segment of the plurality of segments has a leading edge and a second segment of the plurality of segments has a trailing edge, each of the leading edge and trailing edge is configured for operable engagement with one another.

9. The surgical instrument according to claim 8, wherein the first segment and the second segment pivot with respect to one another when the tool assembly is articulated.

10. The surgical instrument according to claim 1, wherein the band includes at least one flange, at least one of the plurality of segments has a recess, and the flange is connected to the recess.

11. The surgical instrument according to claim 1, wherein the plurality of segments extend parallel along the flexible band.

12. The surgical instrument according to claim 1, wherein the segments are aligned in an end to end relationship along the flexible band.

* * * * *